(12) United States Patent
Henriksson et al.

(10) Patent No.: US 7,354,940 B2
(45) Date of Patent: Apr. 8, 2008

(54) 2,5-DIOXOIMIDAZOLIDIN-4-YL ACETAMINES AND ANALOGUES AS INHIBITORS OF METALLOPROTEINASE MMP12

(75) Inventors: Krister Henriksson, Lund (SE); Magnus Munck Af Rosenschöld, Lund (SE)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 10/525,640

(22) PCT Filed: Aug. 26, 2003

(86) PCT No.: PCT/SE03/01328

§ 371 (c)(1),
(2), (4) Date: Feb. 25, 2005

(87) PCT Pub. No.: WO2004/020415

PCT Pub. Date: Mar. 11, 2004

(65) Prior Publication Data

US 2005/0245586 A1    Nov. 3, 2005

(30) Foreign Application Priority Data

Aug. 27, 2002 (SE) .................................... 0202539

(51) Int. Cl.
| | | |
|---|---|---|
| *A61K 31/4439* | (2006.01) | |
| *A61K 31/4166* | (2006.01) | |
| *A61K 31/381* | (2006.01) | |
| *C07D 213/30* | (2006.01) | |
| *C07D 233/40* | (2006.01) | |
| *C07D 409/00* | (2006.01) | |

(52) U.S. Cl. .................... 514/345; 514/389; 514/444; 546/290; 548/318.5; 549/59

(58) Field of Classification Search ................ 514/345, 514/389, 444; 546/290; 548/318.5; 549/59
See application file for complete search history.

(56) References Cited

U.S. PATENT DOCUMENTS

| | | | |
|---|---|---|---|
| 2,745,875 A | 5/1956 | Ehrhart et al. | |
| 3,452,040 A | 6/1969 | Langis | |
| 3,529,019 A | 9/1970 | Suh et al. | |
| 3,849,574 A | 11/1974 | Suh et al. | |
| 4,241,073 A | 12/1980 | Jamieson et al. | |
| 4,315,031 A | 2/1982 | Vincent et al. | |
| 5,068,187 A | 11/1991 | Takeichi et al. | |
| 5,246,943 A | 9/1993 | Blankley et al. | |
| 5,308,853 A | 5/1994 | Hodges et al. | |
| 5,521,187 A | 5/1996 | Freyne et al. | |
| 5,804,593 A | 9/1998 | Warpehoski et al. | |
| 5,919,790 A | 7/1999 | Allen et al. | |
| 5,955,435 A | 9/1999 | Baxter et al. | |
| 6,046,214 A | 4/2000 | Kristiansen et al. | |
| 6,048,841 A | 4/2000 | Baxter et al. | |
| 6,114,361 A | 9/2000 | Robinson et al. | |
| 6,159,995 A | 12/2000 | Thorwart et al. | |
| 6,166,041 A | 12/2000 | Cavalla et al. | |
| 6,218,418 B1 | 4/2001 | Pevarello et al. | |
| 6,268,379 B1 | 7/2001 | Xue et al. | |
| 6,277,987 B1 | 8/2001 | Kukkola et al. | |
| 6,291,685 B1 | 9/2001 | Junghans et al. | |
| 6,329,418 B1 | 12/2001 | Cheng et al. | |
| 6,339,101 B1 | 1/2002 | Ross et al. | |
| 6,340,691 B1 | 1/2002 | Levin et al. | |
| 6,429,213 B1 | 8/2002 | Xue et al. | |
| 6,890,915 B2 | 5/2005 | Sheppeck et al. | |
| 6,906,053 B2 | 6/2005 | Sheppeck et al. | |
| 7,078,424 B2 | 7/2006 | Hamilton et al. | |
| 2002/0006920 A1 | 1/2002 | Robinson et al. | |
| 2002/0028835 A1 | 3/2002 | Hu et al. | |
| 2002/0065219 A1 | 5/2002 | Naidu et al. | |
| 2002/0091107 A1 | 7/2002 | Madar et al. | |
| 2003/0130273 A1 | 7/2003 | Sheppeck et al. | |
| 2004/0106659 A1 | 6/2004 | Af Rosenschold | |
| 2004/0110809 A1 | 6/2004 | Lepisto et al. | |
| 2004/0116486 A1 | 6/2004 | Lepisto et al. | |
| 2004/0127528 A1 | 7/2004 | Eriksson et al. | |
| 2004/0138276 A1 | 7/2004 | Eriksson et al. | |
| 2004/0147573 A1 | 7/2004 | Eriksson et al. | |

(Continued)

FOREIGN PATENT DOCUMENTS

| | | |
|---|---|---|
| EP | 212617 | 8/1986 |
| EP | 0486280 | 11/1991 |
| EP | 0640594 A1 | 3/1995 |
| EP | 0709375 | 10/1995 |

(Continued)

OTHER PUBLICATIONS

Nicolet "Interpretation of the Dehydration of Acetylglutamic Acid by Means of Glutamylthiohydantion Derivatives" Journal of the American Chemical Society 1930, 1192-1195.*

STN International, file CAPLUS, accession No. 1994:299315, Document No. 120:299315, Sakamoto, Shuichi et al., "Preparation of pyridylserine derivatives as psychotropics," WO, A1, 9320053, 19931014, See CAS RN 154696-31-8, 154697-48-0.

STN International, file CAPLUS, accession No. 1997:644516, Batty, Craig et al. "Synthesis and exchange reaction of 5-alkyl-2oxo-6-thioxo-1,2,3,6-hexahydropyrimidine-4-carboxylic acids" 7 Journal of Heterocyclic Chemistry (1997), 34:3, 1355-1367.

(Continued)

*Primary Examiner*—Rebecca Anderson
*Assistant Examiner*—Joseph R. Kosack
(74) *Attorney, Agent, or Firm*—Fish & Richardson P.C.

(57) ABSTRACT

The invention provides compounds of formula (I) in which L, X, Y, $Z^1$, $Z^2$, $R^1$, $R^2$, $R^3$ and $G^2$ have the meanings defined in the specification; processes for their preparation; pharmaceutical compositions containing them; a process for preparing the pharmaceutical compositions; and their use in therapy. The compounds of the invention are inhibitors of metalloproteinase MMP12 and are among other things useful for the treatment of obstructive airways diseases, such as asthma and chronic obstructive pulmonary disease (COPD).

16 Claims, No Drawings

U.S. PATENT DOCUMENTS

| | | |
|---|---|---|
| 2004/0152697 A1 | 8/2004 | Chan et al. |
| 2004/0209874 A1 | 10/2004 | Sheppeck et al. |
| 2005/0019994 A1 | 1/2005 | Chang |
| 2005/0026990 A1 | 2/2005 | Eriksson et al. |
| 2005/0171096 A1 | 8/2005 | Sheppeck et al. |
| 2005/0256176 A1 | 11/2005 | Burrows et al. |
| 2006/0063818 A1 | 3/2006 | Burrows et al. |
| 2006/0276524 A1 | 12/2006 | Henriksson et al. |

FOREIGN PATENT DOCUMENTS

| | | |
|---|---|---|
| EP | 1149843 A1 | 10/2001 |
| EP | 1191024 | 3/2002 |
| EP | 1117616 | 4/2003 |
| EP | 02 74 1724 | 3/2004 |
| WO | WO95/14025 | 11/1994 |
| WO | WO 1996/27583 | 9/1996 |
| WO | WO98/50359 | 5/1998 |
| WO | WO99/06361 | 2/1999 |
| WO | WO99/42443 | 2/1999 |
| WO | WO99/24399 | 5/1999 |
| WO | WO 00/09103 | 8/1999 |
| WO | WO 00/35886 | 12/1999 |
| WO | WO99/62880 | 12/1999 |
| WO | WO 00/12477 | 3/2000 |
| WO | WO 00/12478 | 3/2000 |
| WO | WO 00/40577 | 7/2000 |
| WO | WO00/044770 | 8/2000 |
| WO | WO 00/75106 | 12/2000 |
| WO | WO 01/05756 | 1/2001 |
| WO | WO 01/12189 | 2/2001 |
| WO | WO 01/22363 | 3/2001 |
| WO | WO 01/34573 | 5/2001 |
| WO | WO 02/006232 | 1/2002 |
| WO | WO 02/014262 | 2/2002 |
| WO | WO 02/014354 | 2/2002 |
| WO | WO 02/020515 | 3/2002 |
| WO | WO 02/074749 | 9/2002 |
| WO | WO 02/074751 | 9/2002 |
| WO | WO 02/074752 | 9/2002 |
| WO | WO 02/074767 | 9/2002 |
| WO | WO 02074748 | 9/2002 |
| WO | WO 02074750 | 9/2002 |
| WO | WO 02/96426 | 12/2002 |
| WO | WO/02/096426 A1 * | 12/2002 |
| WO | WO 03/040098 | 5/2003 |
| WO | WO 2004/020415 | 3/2004 |
| WO | WO 2004/024060 | 3/2004 |
| WO | WO 2004/024698 | 3/2004 |
| WO | WO 2004/024718 | 3/2004 |
| WO | WO 2004/024721 | 3/2004 |
| WO | WO06/004532 | 1/2006 |
| WO | WO06/004533 | 1/2006 |

OTHER PUBLICATIONS

STN International, file CAPLUS, accession No. 2002-640897, Gooding, Owen W. et al. "Use of Statistical Design of Experiments in the Optimization of Amide Synthesis Utilizing Polystryene-Supported N-Hydroxybenzotriazole Resin" & Journal of Combinatorial Chemistry (2002), 4(6), 576-583.

STN International, File CAPLUS, CAPLUS accession No. 1968:506154, Doc. No. 69:106154, Lora-Tamayo, J. et al.: "Potential anticancer agents, VI. Sulfonic analogs of aspartic acid", & An. Quim. (1968), 64(6), 591-606.

STN International, File CAPLUS, CAPLUS accession No. 1974:463633, Doc. No. 81:63633, Blaha, Ludvik et al.: "5-Methyl-5-phenoxymethyl-hydantoins", & CS 151744, B, 19731119.

STN International, File CAPLUS, CAPLUS accession No. 1988:631020, Doc No. 109:231020, Mitsui Toatsu Chemicals, Inc.: "Process for the preparation of 5-benzylhydantoins as intermediates for aromatic amino acids"; & JP, A2, 63079879, 19880409.

STN International, File CAPLUS, CAPLUS accession No. 1989:173366, Doc. No. 110:173366, Oh, Chang Hyun et al., "Synthesis of new hydantoin-3-acetic acid derivatives", & Bull. Korean Chem. Soc. (1988), 9(4), 231-5.

STN International, File CAPLUS, CAPLUS accession No. 1990:138955, Doc. No. 112:138955, Crooks, Peter A. et al.: "Synthesis of 5-benzoyl-5-phenyl-and-5-(Phenylhydroxymethyl)-5-phenylhydantoins as potential anticonvulsants"; & J. Heterocycl. Chem. (1989), 26(4), 1113-17.

Whittaker et al. "Design and Therapeutic Application of Matrix Metalloproteinase Inhibitors." Chem Rev. 99 (1999), pp. 2735-2776.

Aharony et al. "Pharmacological Characterization of a New Class of Nonpeptide Neurokimin A Antagonists that Demonstrate Species Selectivity." J. Pharmacol. Exp. Ther. 274:3 (1995), pp. 1216-1221.

Aimoto et al. "Synthesis of Carriers of Differing Strokes Radius with Activated Acyl Groups for Use as Reagents in Labeling Membrane Proteins." Journal of Biological Chemistry, vol. 256(10), pp. 5134-5143, 1981.

Chemical Abstracts, vol. 65, 1966, Abstract No. 13684 h, M. Lora-Tamayo et al.: "Potential anticancer agents. I. Glutamine sulfonate analogs", & Anales Real Soc. Espan. Fis. Quim (Madrid), Ser. B. 62(2), 173-86.

Croce, P. et al. "Stereoselective aldol addition of a chirai glycine enloate synthon to heteroaromatic aldehydes." Heterocycles, 52:3 (2000) pp. 1337-1344.

Knabe, J. "Razemate und enantiomere basisch substituierter 5-phenylhdantoine." Pharmazie. 52:12 (1997) pp. 912-919.

Bright et al. "Monoclonal Antibodies as Surrogate Receptors in High Throughput Screen for Compounds that Enhance Insulin Sensitivity." Life Sciences. 61:23 (1997), pp. 2305-2315.

Lora-Tamayo et al. "anticancerousos Potenciales." An. Quim. 64:6 (1968), pp. 591-606.

Michaelides et al., "Recent Advances in Matrix Metalloproteinase Inhibitors Research", Current Pharmaceutical Design 5:787-819 (1999).

Miyake, Toshiaki et al. "Studies on Glycosylation of erythro-Beta-Hydroxy-L-histidine. A Key Step of Blemycin Total Synthesis." Bull. Chem. Soc. Jpn. 59 (1986), pp. 1387-1395.

Mock et al., "Principles of Hydroxamate Inhibition of Metalloproteases: Carboxypeptidase A", Biochemistry 39:13945-13952 (2000).

Nakajima, Riichiro et al. "The utility of 4-(2-thienyl)pyridines as a derivatization reagent for hplc and ce." Analytical Sciences. 7, Supplement 1991, pp. 177-180.

Nicolet, Ben. "Interpretation of the Dehydration of Acetylglutamic acid by Means of Glutamylthiohydantoin Derivatives." Journal of the American Chemical Society, 1930, pp. 1192-1195.

Owa, Takashi et al. "Man-Designed Bleomycins: Significance of the binding Sites as Enzyme Models and of the Stereochemistry of the Linker Moiety." Tetrahedron. 48:7 (1992) pp. 1193-1208.

Peng, Sean X. "Separation and identification of methods for metalloproteinase inhibitors." Joural of Chromatography B. 764 (2001), pp. 59-80.

Saito, Sei-ichi et al. "A new synthesis of deglyco-bleomycine A2 aiming at the total synthesis of bleomycin." Tetrahedron Letters. 23(5) (1982), pp. 529-532.

STN International, file CAPPLUS, accession No. 1978:424767, Raulais, Daniel J.P., "Synthesis and characterization of phenylthiohydantoin derivatives of amino-acids protected in their sid-chain functions, and their application for monitoring olid-phase peptide synthesis," & Journal of Chemical Research, Synopses (1978), p. 11.

Banfield, J. E. et al., "*Heterocyclic Derivatives of Guanidine. Part V. Reaction of Some Glycidic Esters with Guanidines*", The Journal of The Chemical Society, 511:2747-2756, (1963).

Belvisi, M. G. et al., "*The role of matrix metalloproteinases (MMPs) in the patho-physiology of chronic obstructive pulmonary disease (COPD): a therapeutic role for inhibitors of MMPs?*", Inflammation Research, 52:95-100, (2003).

Borchers, Michael T. et al., "*Acrolein-Induced MUC5ac Expression in Rat Airways*", The American Physiological Society, 274:L573-L581, (1998).

Carmeliet, Peter, "*Proteinases in Cardiovascular Aneurysms and Rupture: Targets for Therapy?*", The Journal of Clinical Investigation, 105(11):1519-1520, (2000).

Comber, Robert N. et al., "*5,5-Disubstituted Hydantoins: Syntheses and Anti-HIV Activity*", J. Med. Chem., 35:3567-3572, (1992).

Dahan, Maurice et al., "*Expression of Matrix Metalloproteinases in Healthy and Diseased Human Gingiva*", Journal of Clinical Periodontology, 28:128-136, (2001).

Doherty, Terence M. et al., "*Therapeutic Developments in Matrix Metalloproteinase Inhibition*", Expert Opinion Ther. Patents, 12(5):665-707, (2002).

Elliot, Sarah et al., "*The Clinical Potential of Matrix Metalloproteinase Inhibitors in the Rheumatic Disorders*", Drugs & Aging, 18(2):87-99, (2001).

Gramatica et al., STN International, HCAPLUS Database, Columbus, OH, Accession No. 2002:356947, Reg. No. 36734-19-7.

Hautamaki, R. Dean et al., "*Requirement for Macrophage Elastase for Cigarette Smoke-Induced Emphysema In Mice*", Science, 277:2002-2004, (2002).

Lindy, Otso et al., "*Matrix Metalloproteinase 13 (Collagenase 3) in Human Rheumatoid Synovium Arthritis Rheumatism*," Arthritis and Rheumatism, 40(8):1391-1399, (1997).

Mandal, Malay et al., "*Clinical Implications of Matrix Metalloproteinases*", Molecular and Cellular Biochemistry, 252:305-329, (2003).

Pyo, Robert et al., "*Targeted Gene Disruption of Matrix Metalloproteinase-9 (Gelatinase B) Suppresses Development of Experimental Abdominal Aortic Aneurysms*", The Journal of Clinical Investigation, 105(11):1641-1649, (2000).

Rouis, M. et al., "*Adenovirus-Mediated Overexpression of Tissue Inhibitor of Metalloproteinase-1 Reduces Atherosclerotic Lesions in Apolipoprotein E-Deficient Mice*", Circulation, 100:533-540, (1999).

Wernicke, Dirk et al., "*Cloning of Collagenase 3 from the Synovial Membrane and Its Expression in Rheumatoid Arthritis and Osteoarthritis*", The Journal of Rheumatology, 23:590-595, (1996).

Whittaker, Mark et al., "*Designs and Therapeutic Application of Matrix Metalloproteinase Inhibitors*", Chemical Reviews, 99:2735-2776, (1999).

Aigner, T. et al., "Growth Plate Cartilage as Developmental Model in Osteoarthritis Research - Potentials and Limitations", Current Drug Targets, vol. 8, No. 2, pp. 377-385, (2007).

Fujita, Masaki et al., "The pathogenesis of COPD: Lessons Learned from in vivo Animal Models", Med. Sci Monit., vol. 13, No. 2, RA19-24, (2007).

MacFadyen, Robert J., "Can Matrix Metalloproteinase Inhibitors Provide a Realistic Therapy in Cardiovascular Medicine," Current Opinion in Pharmacology, vol. 7, pp. 171-178, (2007).

PubMed Abstract (provided in enclosed Office Actions) for: Rifkin, B.R. et al, "Blocking Periodontal Disease Progression by Inhibiting Tissue-Destructive Enzymes: A Potential Therapeutic Role for Tetracyclines and Their Chemically-Modified Analogs", Periodontol, 1993 Aug. 64 (8 Suppl), pp. 819-827.

Rifkin, B.R. et al, "Blocking Periodontal Disease Progression by Inhibiting Tissue-Destructive Enzymes: A Potential Therapeutic Role for Tetracyclines and Their Chemically-Modified Analogs", Periodontal, 1993 Aug. 64 (8 Suppl), pp. 819-827.

Wingerchuk, Dean M. et al., "Multiple Sclerosis: Current Pathophysiological Concepts", Biology of Disease, Lab Invest 2001, vol. 81, pp. 263-281.

\* cited by examiner

2,5-DIOXOIMIDAZOLIDIN-4-YL ACETAMINES AND ANALOGUES AS INHIBITORS OF METALLOPROTEINASE MMP12

CROSS-REFERENCE TO RELATED APPLICATIONS

This application is the national phase application under 35 U.S.C. § 371 of PCT International Application No. PCT/SE2003/001328, filed Aug. 26, 2003, which claims priority to Swedish Application Serial No. 0202539-3, filed Aug. 27, 2002.

The present invention relates to novel compounds, processes for their preparation, pharmaceutical compositions containing them and their use in therapy.

Metalloproteinases are a superfamily of proteinases (enzymes) whose numbers in recent years have increased dramatically. Based on structural and functional considerations these enzymes have been classified into families and subfamilies as described in N. M. Hooper (1994) FEBS Letters 354:1–6. Examples of metalloproteinases include the matrix metalloproteinases (MMPs) such as the collagenases (MMP1, MMP8, MMP13), the gelatinases (MMP2, MMP9), the stromelysins (MMP3, MMP10, MMP11), matrilysin (MMP7), metalloelastase (MMP12), enamelysin (MMP19), the MT-MMPs (MMP14, MMP15, MMP16, MMP17); the reprolysin or adamalysin or MDC family which includes the secretases and sheddases such as TNF converting enzymes (ADAM 10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem J. 321:265–279).

Metalloproteinases have been associated with many diseases or conditions. Inhibition of the activity of one or more metalloproteinases may well be of benefit in these diseases or conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as restenosis and atheroscelerosis; asthma; rhinitis; and chronic obstructive pulmonary diseases (COPD).

MMP12, also known as macrophage elastase or metalloelastase, was initially cloned in the mouse by Shapiro et al [1992, Journal of Biological Chemistry 267: 4664] and in man by the same group in 1995. MMP12 is preferentially expressed in activated macrophages, and has been shown to be secreted from alveolar macrophages from smokers [Shapiro et al, 1993, Journal of Biological Chemistry, 268: 23824] as well as in foam cells in atherosclerotic lesions [Matsumoto et al, 1998, Am J Pathol 153: 109]. A mouse model of COPD is based on challenge of mice with cigarette smoke for six months, two cigarettes a day six days a week. Wildtype mice developed pulmonary emphysema after this treatment. When MMP12 knock-out mice were tested in this model they developed no significant emphysema, strongly indicating that MMP12 is a key enzyme in the COPD pathogenesis. The role of MMPs such as MMP12 in COPD (emphysema and bronchitis) is discussed in Anderson and Shinagawa, 1999, Current Opinion in Anti-inflammatory and Immunomodulatory Investigational Drugs 1(1): 29–38. It was recently discovered that smoking increases macrophage infiltration and macrophage-derived MMP-12 expression in human carotid artery plaques Kangavari [Matetzky S, Fishbein M C et al., Circulation 102:(18), 36–39 Suppl. S, Oct. 31, 2000].

A number of metalloproteinase inhibitors are known (see for example the reviews of MMP inhibitors by Beckett R. P. and Whittaker M., 1998, Exp. Opin. Ther. Patents, 8(3): 259–282, and by Whittaker M. et al, 1999, Chemical Reviews 99(9):2735–2776).

Published International Patent Application No. WO 02/096426 (Bristol-Myers Squibb Company) describes hydantoin derivatives of formula

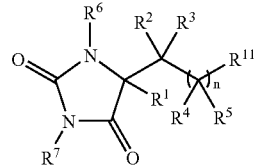

in which the substituents $R^1$, $R^2$, $R^3$, $R^4$, $R^5$, $R^6$, $R^7$, and $R^{11}$ are broadly defined. The derivatives are said, in general terms, to act as inhibitors of metalloproteinases, in particular TACE, MMPs and/or aggrecanase, although no data demonstrating biological is activity is included in the application.

We have now discovered a new class of compounds that are potent and selective MMP12 inhibitors and have desirable activity profiles, in particular they are highly selective inhibitors for MMP12 relative to, for example, MMP14, MMP19 and TACE.

In accordance with the present invention, there is therefore provided a compound of formula (I) or a pharmaceutically acceptable salt or solvate thereof

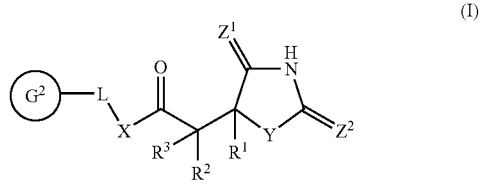

(I)

wherein
X represents an oxygen atom or a group $NR^4$ or $CH_2$;
Y represents NH or N-methyl;

$Z^1$ and $Z^2$ each independently represent an oxygen or sulphur atom, provided that at least one of $Z^1$ and $Z^2$ represents an oxygen atom;

Either $R^1$ represents hydrogen or a group selected from $C_1$–$C_6$ alkyl and a saturated or unsaturated 3- to 10-membered ring system which may comprise at least one ring heteroatom selected from nitrogen, oxygen and sulphur, each group being optionally substituted with at least one substituent selected from halogen, hydroxyl, cyano, carboxyl, —$NR^5R^6$, —$CONR^7R^8$, $C_1$–$C_6$ alkyl, $C_1$–$C_6$ alkoxy, $C_1$–$C_6$ alkylcarbonyl(oxy), —$S(O)_m C_1$–$C_6$ alkyl where m is 0, 1 or 2, $C_1$–$C_6$ alkylsulphonylamino, $C_1$–$C_6$ alkoxycarbonyl(amino), benzyloxy and a saturated or unsaturated 5- to 6-membered ring which may comprise at least one ring heteroatom selected from nitrogen, oxygen and sulphur, the ring in turn being optionally substituted with at least one substituent selected from halogen, hydroxyl, oxo (=O), carboxyl, cyano, $C_1$–$C_6$ alkyl, $C_1$–$C_6$ alkoxycarbonyl and $C_1$–$C_6$ hydroxyalkyl, $R^2$ represents hydrogen or $C_1$–$C_6$ alkyl, and $R^3$ represents hydrogen or $C_1$–$C_6$ alkyl, or $R^1$ and $R^2$ together with the carbon atoms to which they are attached form a saturated 5- to 6-membered ring optionally comprising a ring heteroatom selected from nitrogen, oxygen and sulphur, and $R^3$ is as defined above, or $R^2$ and $R^3$ together with the carbon atom to which they are attached form a saturated 5- to 6-membered ring optionally comprising a ring heteroatom selected from nitrogen, oxygen and sulphur, and $R^1$ is as defined above;

$R^4$ represents hydrogen or $C_1$–$C_6$ alkyl;

$R^5$, $R^6$, $R^7$ and $R^8$ each independently represent hydrogen or $C_1$–$C_6$ alkyl optionally substituted by at least one substituent selected from hydroxyl, halogen and $C_1$–$C_6$ alkoxy;

L represents —$CH_2C(O)$— or —$C(O)CH_2$—, or

L represents a $C_2$–$C_6$ alkyl or $C_2$–$C_6$ alkynyl group optionally interrupted or terminated by at least one moiety selected from O, NH, S, SO, $SO_2$ and C(O), or L represents a $C_3$–$C_6$ cycloalkyl, methyl$C_3$–$C_6$ cycloalkyl or $C_3$–$C_6$ cycloalkylmethyl group, each of the recited groups being optionally substituted with at least one substituent selected from hydroxyl, halogen, $C_1$–$C_4$ alkyl, $C_1$–$C_4$ haloalkyl, $C_1$–$C_4$ alkoxy and $C_1$–$C_4$ haloalkoxy, or L represents a $C_3$–$C_4$ alkylene chain, the ends of which are attached to adjacent ring carbon atoms in the 5- to 10-membered ring system of $G^2$ to form a ring;

$G^2$ represents a saturated or unsaturated 5- to 10-membered ring system which may comprise at least one ring heteroatom selected from nitrogen, oxygen and sulphur, the ring system being optionally substituted with at least one substituent selected from halogen, hydroxyl, cyano, nitro, $C_1$–$C_6$ alkyl (optionally substituted by one or more of cyano, halogen, hydroxyl and methoxy), $C_2$–$C_6$ alkenyl, $C_1$–$C_6$ alkoxy (optionally substituted by one or more halogen atoms), —$S(O)_n C_1$–$C_6$ alkyl where n is 0, 1 or 2, $C_1$–$C_6$ alkylcarbonyl (amino), $C_1$–$C_6$ alkylcarbonyloxy, phenyl, benzyloxy, —$NR^9R^{10}$ and a group of formula

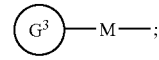

(II)

$R^9$ and $R^{10}$ each independently represent hydrogen or $C_1$–$C_6$ alkyl optionally substituted by at least one substituent selected from hydroxyl, halogen and $C_1$–$C_6$ alkoxy;

M represents a bond or —O—, —S—, —C≡C—, —$CH_2O$— or —$OCH_2$—;

$G^3$ represents an unsaturated 5- to 10-membered ring system which may comprise at least one ring heteroatom selected from nitrogen, oxygen and sulphur, the ring system being optionally substituted with at least one substituent selected from halogen, hydroxyl, cyano, nitro, $C_1$–$C_6$ alkyl (optionally substituted by one or more of cyano, halogen, hydroxyl and methoxy), $C_2$–$C_6$ alkenyl, $C_1$–$C_6$ alkoxy (optionally substituted by one or more halogen atoms), —$S(O)_t C_1$–$C_6$ alkyl where t is 0, 1 or 2, $C_1$–$C_6$ alkylcarbonyl(amino), $C_1$–$C_6$ alkylcarbonyloxy, phenyl, benzyloxy and —$NR^{11}R^{12}$; and $R^{11}$ and $R^{12}$ each independently represent hydrogen or $C_1$–$C_6$ alkyl optionally substituted by at least one substituent selected from hydroxyl, halogen and $C_1$–$C_6$ alkoxy.

In the context of the present specification, unless otherwise stated, an alkyl, alkenyl or alkynyl substituent group or an alkyl moiety in a substituent group may be linear or branched. A haloalkyl or haloalkoxy substituent group will comprise at least one halogen atom, e.g. one, two, three or four halogen atoms. A hydroxyalkyl substituent may contain one or more hydroxyl groups but preferably contains one or two hydroxyl groups. When $R^1$ and $R^2$, or $R^2$ and $R^3$, form a ring, it should be understood that the ring may comprise up to one ring heteroatom only. In the definition of $R^1$, it should be noted that each of the saturated or unsaturated 3- to 10-membered ring system and the saturated or unsaturated 5- to 6-membered ring may have alicyclic or aromatic properties. The same comment applies to the saturated or unsaturated 5- to 10-membered ring system in the definition of $G^2$. An unsaturated ring system will be partially or fully unsaturated. When L represents a $C_2$–$C_6$ alkyl or $C_2$–$C_6$ alkynyl group optionally interrupted or terminated by more than one moiety (e.g. two moieties) selected from O, NH, S, SO, $SO_2$ and C(O), it may in some instances be possible for the two moieties to be adjacent to one another but otherwise the moieties will need to be separated by one or more carbon atoms. For example, whilst it is acceptable for C(O) or $SO_2$ and NH to be adjacent to one another, combinations such as NH—NH, NH—O, O—O, O—SO, O—$SO_2$, SO—SO, $SO_2$—$SO_2$ and so on are undesirable. The person skilled in the art will know which moieties may be placed next to one another.

In an embodiment of the invention, X represents an oxygen atom or a group $NR^4$ where $R^4$ represents hydrogen or $C_1$–$C_6$, preferably $C_1$–$C_4$, alkyl (e.g. methyl, ethyl, n-propyl, isopropyl, n-butyl, isobutyl, tert-butyl, n-pentyl or n-hexyl).

In another embodiment of the invention, X represents NH or N-methyl. In a further embodiment, X represents NH.

In one embodiment, $Z^1$ and $Z^2$ both represent an oxygen atom.

In an embodiment of the invention, $R^1$ represents hydrogen or a group selected from $C_1$–$C_6$, preferably $C_1$–$C_4$, alkyl (e.g. methyl, ethyl, n-propyl, isopropyl, n-butyl, isobutyl, tert-butyl, n-pentyl or n-hexyl) and a saturated or unsaturated 3- to 10-membered ring system which may comprise at least one ring heteroatom (e.g. one, two, three or four ring heteroatoms independently) selected from nitrogen, oxygen and sulphur, each group being optionally substituted with at least one substituent (e.g. one, two, three or four substituents independently) selected from halogen (e.g. chlorine, fluorine, bromine or iodine), hydroxyl, cyano, carboxyl, —$NR^5R^6$, —$CONR^7R^8$, $C_1$–$C_6$, preferably $C_1$–$C_4$, alkyl (e.g. methyl, ethyl, n-propyl, isopropyl, n-butyl, isobutyl, tert-butyl, n-pentyl or n-hexyl), $C_1$–$C_6$, preferably $C_1$–$C_4$, alkoxy (e.g. methoxy, ethoxy, n-propoxy or n-butoxy), $C_1$–$C_6$, preferably $C_1$–$C_4$, alkylcarbonyl(oxy) (e.g. methylcarbonyl(oxy), ethylcarbonyl(oxy), n-propylcarbonyl(oxy), isopropylcarbonyl(oxy), n-butylcarbonyl(oxy), n-pentylcarbonyl(oxy) or n-hexylcarbonyl(oxy)), —$S(O)_mC_1$–$C_6$, preferably $C_1$–$C_4$, alkyl where m is 0, 1 or 2 (e.g. methylthio, ethylthio, methylsulphinyl, ethylsulphinyl, methylsulphonyl or ethylsulphonyl), $C_1$–$C_6$, preferably $C_1$–$C_4$, alkylsulphonylamino (e.g. methylsulphonylamino, ethylsulphonylamino, n-propylsulphonylamino, isopropylsulphonylamino, n-butylsulphonylamino, n-pentylsulphonylamino or n-hexylsulphonylamino), $C_1$–$C_6$, preferably $C_1$–$C_4$, alkoxycarbonyl(amino) (e.g. methoxycarbonyl(amino), ethoxycarbonyl(amino), n-propoxycarbonyl(amino) or n-butoxycarbonyl(amino)), benzyloxy and a saturated or unsaturated 5- to 6-membered ring which may comprise at least one ring heteroatom (e.g. one, two, three or four ring heteroatoms independently) selected from nitrogen, oxygen and sulphur, the ring in turn being optionally substituted with at least one substituent (e.g. one, two or three substituents independently) selected from halogen (e.g. chlorine, fluorine, bromine or iodine), hydroxyl, oxo, carboxyl, cyano, $C_1$–$C_6$, preferably $C_1$–$C_4$, alkyl (e.g. methyl, ethyl, n-propyl, isopropyl, n-butyl, isobutyl, tert-butyl, n-pentyl or n-hexyl), $C_1$–$C_6$, preferably $C_1$–$C_4$, alkoxycarbonyl (e.g. methoxycarbonyl or ethoxycarbonyl) and $C_1$–$C_6$, preferably $C_1$–$C_4$, hydroxyalkyl (e.g. —$CH_2OH$, —$CH_2CH_2OH$, —$CH_2CH_2CH_2OH$ or —$CH(OH)CH_3$); $R^2$ represents hydrogen or $C_1$–$C_6$, preferably $C_1$–$C_4$, alkyl (e.g. methyl, ethyl, n-propyl, isopropyl, n-butyl, isobutyl, tert-butyl, n-pentyl or n-hexyl); and $R^3$ represents hydrogen or $C_1$–$C_6$, preferably $C_1$–$C_4$, alkyl (e.g. methyl, ethyl, n-propyl, isopropyl, n-butyl, isobutyl, tert-butyl, n-pentyl or n-hexyl).

Examples of saturated or unsaturated 3- to 10-membered ring systems that may be used, which may be monocyclic or polycyclic (e.g. bicyclic) in which the two or more rings are fused, include one or more (in any combination) of cyclopropyl, cyclobutyl, cyclopentyl, cyclohexyl, bicyclo[2.2.1]heptyl, cyclopentenyl, cyclohexenyl, phenyl, pyrrolidinyl, piperidinyl, piperazinyl, morpholinyl, thiomorpholinyl, diazabicyclo[2.2.1]hept-2-yl, naphthyl, benzofuranyl, benzothienyl, benzodioxolyl, quinolinyl, 2,3-dihydrobenzofuranyl, tetrahydropyranyl, pyrazolyl, pyrazinyl, thiazolidinyl, indanyl, thienyl, isoxazolyl, pyridazinyl, thiadiazolyl, pyrrolyl, furanyl, thiazolyl, indolyl, imidazolyl, pyrimidinyl, benzimidazolyl, triazolyl, tetrazolyl and pyridinyl. Preferred ring systems include phenyl, pyridinyl and tetrahydropyranyl.

Examples of saturated or unsaturated 5- to 6-membered ring substituents in $R^1$ include cyclopentyl, cyclohexyl, phenyl, pyrrolidinyl, piperidinyl, piperazinyl, morpholinyl, tetrahydropyranyl, thiomorpholinyl, pyrazolyl, pyrazinyl, pyridazinyl, thiazolidinyl, thienyl, isoxazolyl, pyrimidinyl, thiadiazolyl, pyrrolyl, furanyl, thiazolyl, imidazolyl, triaz-olyl, tetrazolyl and pyridinyl. Preferred rings include morpholinyl, pyrimidinyl, phenyl, imidazolyl, piperidinyl, tetrahydropyranyl and triazolyl.

Particular values for $R^1$ include the following:

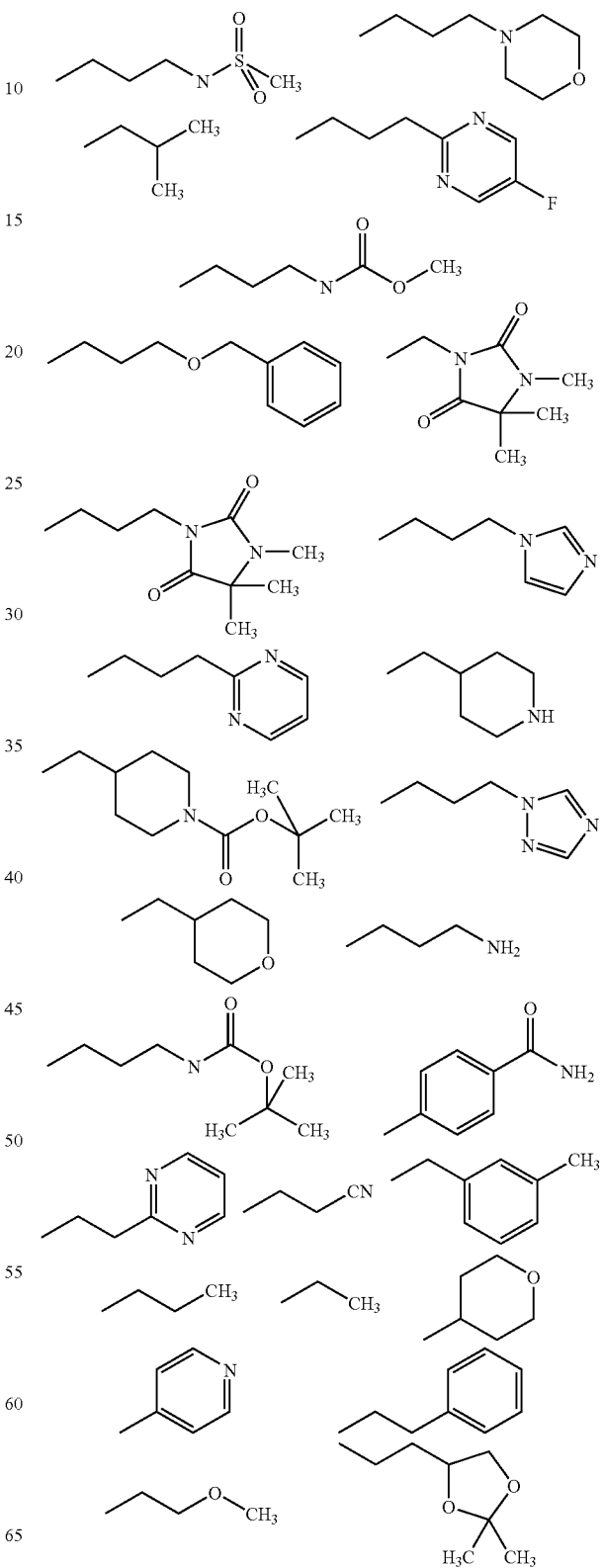

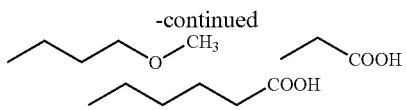

In another embodiment of the invention, $R^1$ represents hydrogen or a group selected from $C_1$–$C_4$ alkyl and a saturated or unsaturated 5- to 10-membered ring system which may comprise at least one ring heteroatom (e.g. one, two, three or four ring heteroatoms independently) selected from nitrogen, oxygen and sulphur, each group being optionally substituted with at least one substituent (e.g. one, two, three or four substituents independently) selected from halogen, hydroxyl, cyano, carboxyl, —$NR^5R^6$, —$CONR^7R^8$, $C_1$–$C_4$ alkyl, $C_1$–$C_4$ alkoxy, $C_1$–$C_4$ alkylcarbonyl(oxy), —$S(O)_mC_1$–$C_4$ alkyl where m is 0, 1 or 2, $C_1$–$C_4$ alkylsulphonylamino, $C_1$–$C_4$ alkoxycarbonyl(amino), benzyloxy and a saturated or unsaturated 5- to 6-membered ring which may comprise at least one ring heteroatom (e.g. one, two, three or four ring heteroatoms independently) selected from nitrogen, oxygen and sulphur, the ring in turn being optionally substituted with at least one substituent (e.g. one, two or three substituents independently) selected from halogen, hydroxyl, oxo, carboxyl, cyano, $C_1$–$C_4$ alkyl $C_1$–$C_4$ alkoxycarbonyl and $C_1$–$C_4$ hydroxyalkyl;

$R^2$ represents hydrogen or $C_1$–$C_4$ alkyl; and $R^3$ represents hydrogen or $C_1$–$C_4$ alkyl.

In still another embodiment, $R^1$ represents hydrogen or $C_1$–$C_4$ alkyl, particularly methyl;

$R^2$ represents hydrogen; and $R^3$ represents hydrogen.

Alternatively, $R^1$ and $R^2$ may together with the carbon atoms to which they are attached form a saturated 5- to 6-membered ring optionally comprising a ring heteroatom selected from nitrogen, oxygen and sulphur (e.g. cyclopentyl, cyclohexyl, pyrrolidinyl, piperidinyl, tetrahydrofuranyl or tetrahydrothiophenyl), and $R^3$ is as previously defined.

As a further alternative, $R^2$ and $R^3$ may together with the carbon atom to which they are attached form a saturated 5- to 6-membered ring optionally comprising a ring heteroatom selected from nitrogen, oxygen and sulphur (e.g. cyclopentyl, cyclohexyl, pyrrolidinyl, piperidinyl, tetrahydrofuranyl or tetrahydrothiophenyl), and $R^1$ is as previously defined.

$R^5$, $R^6$, $R^7$ and $R^8$ each independently represent hydrogen or $C_1$–$C_6$, preferably $C_1$–$C_4$, alkyl (e.g. methyl, ethyl, n-propyl, isopropyl, n-butyl, isobutyl, tert-butyl, n-pentyl or n-hexyl) optionally substituted by at least one substituent (e.g. one, two or three substituents independently) selected from hydroxyl, halogen (e.g. chlorine, fluorine, bromine or iodine) and $C_1$–$C_6$, preferably $C_1$–$C_4$, alkoxy (e.g. methoxy, ethoxy, n-propoxy or n-butoxy).

In an embodiment of the invention, $R^5$, $R^6$, $R^7$ and $R^8$ each independently represent hydrogen or $C_1$–$C_6$, preferably $C_1$–$C_4$, alkyl. In another embodiment, $R^5$, $R^6$, $R^7$ and $R^8$ each independently represent hydrogen.

L represents —$CH_2C(O)$— or —$C(O)CH_2$—, or

L represents a $C_2$–$C_6$, preferably $C_2$–$C_4$, alkyl or $C_2$–$C_6$, preferably $C_2$–$C_4$, alkynyl group optionally interrupted or terminated by at least one moiety (e.g. one or two moieties independently) selected from O, NH, S, SO, $SO_2$ and C(O) (for example, —$(CH_2)_2$—, —$(CH_2)_3$—, —$(CH_2)_4$—, —$(CH_2)_5$—, —$(CH_2)_6$—, —C≡C—, —$CH_2$—C≡C—, —C≡C—$CH_2$—, —O—$(CH_2)_3$—NH—, —NH—$(CH_2)_3$—O—, —$CH(CH_3)$—, —$(CH_2)_2$—C(O)—, —C(O)—$(CH_2)_2$—, —$CH_2CH(CH_3)$—, —$CH(CH_3)CH_2$—, —$(CH_2)_2$—O—$CH_2$— or —$CH_2$—O—$(CH_2)_2$), or L represents a $C_3$–$C_6$ cycloalkyl (cyclopropyl, cyclobutyl, cyclopentyl or cyclohexyl), methyl$C_3$–$C_6$ cycloalkyl (e.g. methylcyclopropyl) or $C_3$–$C_6$ cycloalkylmethyl (e.g. cyclopropylmethyl) group, each of the recited groups being optionally substituted with at least one substituent (e.g. one, two or three substituents independently) selected from hydroxyl, halogen (e.g. chlorine, fluorine, bromine or iodine), $C_1$–$C_4$, preferably $C_1$–$C_2$, alkyl (e.g. methyl, ethyl, n-propyl, isopropyl, n-butyl or t-butyl), $C_1$–$C_4$, preferably $C_1$–$C_2$, haloalkyl (e.g. trifluoromethyl or pentafluoroethyl), $C_1$–$C_4$, preferably $C_1$–$C_4$, alkoxy (e.g. methoxy or ethoxy) and $C_1$–$C_4$, preferably $C_1$–$C_2$, haloalkoxy (e.g. trifluoromethoxy) (such as —$CH_2OCH(R)CH_2NH$— or —$NHCH_2CH(R)OCH_2$— where R represents methyl, hydroxyl or methoxy, —$CH(CH_3)$—$CH(OH)$—, —$CH(OH)$—$CH(CH_3)$—, —$CH_2CH(OH)$—, —$CH(OH)CH_2$—, —$CH_2CH(OCH_3)$— or —$CH(OCH_3)CH_2$—), or L represents a $C_3$–$C_4$ alkylene chain, the ends of which are attached to adjacent ring carbon atoms in the 5- to 10-membered ring system of $G^2$ to form a ring (for example, if $G^2$ represents an unsubstituted phenyl group and L represents a $C_3$ alkylene chain, $G^2$ and L together form a 2,3-dihydroinden-2-yl group having the structure:

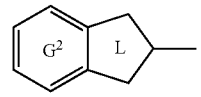

In an embodiment of the invention, reading from left to right in formula (I),

L represents —$C(O)CH_2$—, or

L represents $C_2$–$C_4$ alkyl optionally interrupted or terminated by an oxygen atom, cyclopropyl or cyclopropylmethyl, each of which is optionally substituted with one or two substituents independently selected from hydroxyl, halogen, methyl, trifluoromethyl, methoxy and trifluoromethoxy, or L represents a $C_3$–$C_4$ alkylene chain, the ends of which are attached to adjacent ring carbon atoms in the 5- to 10-membered ring system of $G^2$ to form a ring.

In a further embodiment of the invention, L represents (reading from left to right in formula (I)) —$C(O)CH_2$—, —$(CH_2)_2$—, —$CH(CH_3)$—, —$CH(CH_3)CH_2$—, —$CH(OH)$—$CH(CH_3)$—, —$CH(OH)CH_2$—, —$CH(OCH_3)CH_2$—, —$CH_2$—O—$(CH_2)_2$, cyclopropyl, cyclopropylmethyl, or L represents a $C_3$ alkylene chain, the ends of which are attached to adjacent ring carbon atoms in the 5- to 10-membered ring system of $G^2$ to form a ring.

$G^2$ represents a saturated or unsaturated 5- to 10-membered ring system which may comprise at least one ring heteroatom (e.g. one, two, three or four ring heteroatoms independently) selected from nitrogen, oxygen and sulphur, the ring system being optionally substituted with at least one substituent (e.g. one, two, three or four substituents independently) selected from halogen (e.g. chlorine, fluorine, bromine or iodine), hydroxyl, cyano, nitro, $C_1$–$C_6$, preferably $C_1$–$C_4$, alkyl such as methyl, ethyl, n-propyl, isopropyl, n-butyl, isobutyl, tert-butyl, n-pentyl or n-hexyl (optionally substituted by one or more, e.g. one, two or three, substituents independently selected from cyano, halogen such as chlorine, fluorine, bromine or iodine, hydroxyl and methoxy), $C_2$–$C_6$, preferably $C_2$–$C_4$, alkenyl (e.g. ethenyl, prop-1-enyl, prop-2-enyl, but-1-enyl, pent-1-enyl, hex-1-enyl or 2-methyl-pent-2-enyl), $C_1$–$C_6$, preferably $C_1$–$C_4$, alkoxy such as methoxy, ethoxy, n-propoxy or n-butoxy (optionally substituted by one or more, e.g. one, two or three, halogen atoms such as chlorine, fluorine, bromine or iodine), —S(O)$_n$$C_1$–$C_6$, preferably $C_1$–$C_4$, alkyl where n is 0, 1 or 2 (e.g. methylthio, ethylthio, methylsulphinyl, ethylsulphinyl, methylsulphonyl or ethylsulphonyl), $C_1$–$C_6$, preferably $C_1$–$C_4$, alkylcarbonyl(amino) (e.g. methylcarbonyl(amino), ethylcarbonyl(amino), n-propylcarbonyl(amino), isopropylcarbonyl(amino), n-butylcarbonyl(amino), n-pentylcarbonyl(amino) or n-hexylcarbonyl(amino)), $C_1$–$C_6$, preferably $C_1$–$C_4$, alkylcarbonyloxy (e.g. methylcarbonyloxy, ethylcarbonyloxy, n-propylcarbonyloxy, isopropylcarbonyloxy, n-butylcarbonyloxy, n-pentylcarbonyloxy or n-hexylcarbonyloxy), phenyl, benzyloxy, —NR$^9$R$^{10}$ and a group of formula

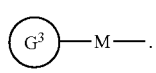

(II)

Examples of saturated or unsaturated 5- to 10-membered ring systems that may be used in $G^2$, which may be monocyclic or polycyclic (e.g. bicyclic) in which the two or more rings are fused, include one or more (in any combination) of cyclopentyl, cyclohexyl, bicyclo[2.2.1]heptyl, cyclopentenyl, cyclohexenyl, phenyl, pyrrolidinyl, piperidinyl, piperazinyl, morpholinyl, thiomorpholinyl, diazabicyclo[2.2.1]hept-2-yl, naphthyl, benzofuranyl, benzothienyl, benzodioxolyl, quinolinyl, 2,3-dihydrobenzofuranyl, tetrahydropyranyl, pyrazolyl, pyrazinyl, thiazolidinyl, indanyl, thienyl, isoxazolyl, pyridazinyl, thiadiazolyl, pyrrolyl, furanyl, thiazolyl, indolyl, imidazolyl, pyrimidinyl, benzimidazolyl, triazolyl, tetrazolyl and pyridinyl. Preferred ring systems include phenyl, indolyl, thienyl and piperidinyl.

R$^9$ and R$^{10}$ each independently represent hydrogen or $C_1$–$C_6$, preferably $C_1$–$C_4$, alkyl (e.g. methyl, ethyl, n-propyl, isopropyl, n-butyl, isobutyl, tert-butyl, n-pentyl or n-hexyl) optionally substituted by at least one substituent (e.g. one, two or three substituents independently) selected from hydroxyl, halogen (e.g. chlorine, fluorine, bromine or iodine) and $C_1$–$C_6$, preferably $C_1$–$C_4$, alkoxy (e.g. methoxy, ethoxy, n-propoxy or n-butoxy).

In an embodiment of the invention, $G^2$ represents a saturated or unsaturated 5- to 9-membered ring system which may comprise one ring heteroatom selected from nitrogen, oxygen and sulphur, the ring system being optionally substituted with one or two substituents independently selected from halogen, hydroxyl, cyano, nitro, $C_1$–$C_4$ alkyl (optionally substituted by one or more, e.g. one, two or three, substituents independently selected from cyano, halogen such as chlorine, fluorine, bromine or iodine, hydroxyl and methoxy), $C_2$–$C_4$ alkenyl, $C_1$–$C_4$ alkoxy (optionally substituted by one or more, e.g. one, two or three, halogen atoms such as chlorine, fluorine, bromine or iodine), —S(O)$_n$$C_1$–$C_4$ alkyl where n is 0, 1 or 2, $C_1$–$C_4$ alkylcarbonyl(amino), $C_1$–$C_4$ alkylcarbonyloxy, phenyl, benzyloxy, —NR$^9$R$^{10}$ and a group of formula

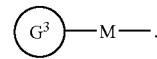

(II)

In another embodiment, $G^2$ represents a saturated or unsaturated 5- to 9-membered ring system which may comprise one ring heteroatom selected from nitrogen and sulphur (e.g. phenyl, indolyl, thienyl or piperidinyl), the ring system being optionally substituted with one or two substituents independently selected from halogen, $C_1$–$C_4$ alkyl and a group of formula

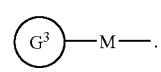

(II)

In an embodiment of the invention, M represents a bond, —O— or —C≡C—. In a further embodiment, M represents a bond.

$G^3$ represents an unsaturated 5- to 10-membered ring system which may comprise at least one ring heteroatom (e.g. one, two, three or four ring heteroatoms independently) selected from nitrogen, oxygen and sulphur, the ring system being optionally substituted with at least one substituent (e.g. one, two, three or four substituents independently) selected from halogen (e.g. chlorine, fluorine, bromine or iodine), hydroxyl, cyano, nitro, $C_1$–$C_6$, preferably $C_1$–$C_4$, alkyl such as methyl, ethyl, n-propyl, isopropyl, n-butyl, isobutyl, tert-butyl, n-pentyl or n-hexyl (optionally substituted by one or more, e.g. one, two or three, substituents independently selected from cyano, halogen such as chlorine, fluorine, bromine or iodine, hydroxyl and methoxy), $C_2$–$C_6$, preferably $C_2$–$C_4$, alkenyl (e.g. ethenyl, prop-1-enyl, prop-2-enyl, but-1-enyl, pent-1-enyl, hex-1-enyl or 2-methyl-pent-2-enyl), $C_1$–$C_6$, preferably $C_1$–$C_4$, alkoxy such as methoxy, ethoxy, n-propoxy or n-butoxy (optionally substituted by one or more, e.g. one, two or three, halogen atoms such as chlorine, fluorine, bromine or iodine), —S(O)$_t$$C_1$–$C_6$, preferably $C_1$–$C_4$, alkyl where t is 0, 1 or 2 (e.g. methylthio, ethylthio, methylsulphinyl, ethylsulphinyl, methylsulphonyl or ethylsulphonyl), $C_1$–$C_6$, preferably $C_1$–$C_4$, alkylcarbonyl(amino) (e.g. methylcarbonyl(amino), ethylcarbonyl(amino), n-propylcarbonyl(amino), isopropylcarbonyl(amino), n-butylcarbonyl(amino), n-pentylcarbonyl(amino) or n-hexylcarbonyl(amino)), $C_1$–$C_6$, preferably $C_1$–$C_4$, alkylcarbonyloxy (e.g. methylcarbonyloxy, ethylcarbonyloxy, n-propylcarbonyloxy, isopropylcarbonyloxy, n-butylcarbonyloxy, n-pentylcarbonyloxy or n-hexylcarbonyloxy), phenyl, benzyloxy and —NR$^{11}$R$^{12}$.

Examples of unsaturated 5- to 10-membered ring systems that may be used in $G^3$, which may be monocyclic or polycyclic (e.g. bicyclic) in which the two or more rings are fused, include one or more (in any combination) of cyclopentenyl, cyclohexenyl, phenyl, naphthyl, benzofuranyl, benzothienyl, benzodioxolyl, quinolinyl, 2,3-dihydrobenzofuranyl, pyrazolyl, pyrazinyl, thiazolidinyl, indanyl, thienyl, isoxazolyl, pyridazinyl, thiadiazolyl, pyrrolyl, furanyl, thiazolyl, indolyl, imidazolyl, pyrimidinyl, benzimidazolyl, triazolyl, tetrazolyl and pyridinyl. Preferred ring systems include phenyl, thienyl, naphthyl, benzofuranyl, benzothienyl, pyridinyl, pyrrolyl, furanyl, benzodioxolyl, quinolinyl and 2,3-dihydrobenzofuranyl.

$R^{11}$ and $R^{12}$ each independently represent hydrogen or $C_1$–$C_6$, preferably $C_1$–$C_4$, alkyl (e.g. methyl, ethyl, n-propyl, isopropyl, n-butyl, isobutyl, tert-butyl, n-pentyl or n-hexyl) optionally substituted by at least one substituent (e.g. one, two or three substituents independently) selected from hydroxyl, halogen (e.g. chlorine, fluorine, bromine or iodine) and $C_1$–$C_6$, preferably $C_1$–$C_4$, alkoxy (e.g. methoxy, ethoxy, n-propoxy or n-butoxy).

In one embodiment, $G^3$ represents an unsaturated 5- to 10-membered ring system which may comprise one or two ring heteroatoms independently selected from nitrogen, oxygen and sulphur (e.g. phenyl, thienyl, naphthyl, benzofuranyl, benzothienyl, pyridinyl, pyrrolyl, furanyl, benzodioxolyl, quinolinyl and 2,3-dihydrobenzofuranyl), the ring system being optionally substituted with one or two substituents independently selected from halogen, hydroxyl, cyano, nitro, $C_1$–$C_4$ alkyl (optionally substituted by one or more, e.g. one, two or three, substituents independently selected from cyano, halogen such as chlorine, fluorine, bromine or iodine, hydroxyl and methoxy), $C_2$–$C_4$ alkenyl, $C_1$–$C_4$ alkoxy (optionally substituted by one or more, e.g. one, two or three, halogen atoms such as chlorine, fluorine, bromine or iodine), —S(O)$_t$$C_1$–$C_4$ alkyl where t is 0, 1 or 2, $C_1$–$C_4$ alkylcarbonyl(amino), $C_1$–$C_4$ alkylcarbonyloxy, phenyl, benzyloxy and —NR$^{11}$R$^{12}$ In another embodiment, $G^3$ represents an unsaturated 5- to 10-membered ring system which may comprise one or two ring heteroatoms independently selected from nitrogen, oxygen and sulphur (e.g. phenyl, thienyl, naphthyl, benzofuranyl, benzothienyl, pyridinyl, pyrrolyl, furanyl, benzodioxolyl, quinolinyl and 2,3-dihydrobenzofuranyl), the ring system being optionally substituted with one or two substituents independently selected from halogen, cyano, nitro, $C_1$–$C_4$ alkyl (optionally substituted by one or more, e.g. one, two or three, substituents independently selected from cyano and halogen), $C_1$–$C_4$ alkoxy (optionally substituted by one or more, e.g. one, two or three, halogen atoms), $C_1$–$C_4$ alkylthio, $C_1$–$C_4$ alkylcarbonyl(amino), phenyl and benzyloxy.

In still another embodiment, $G^3$ represents an unsaturated 5- to 10-membered ring system which may comprise one or two ring heteroatoms independently selected from nitrogen, oxygen and sulphur (e.g. phenyl, thienyl, naphthyl, benzofuranyl, benzothienyl, pyridinyl, pyrrolyl, furanyl, benzodioxolyl, quinolinyl and 2,3-dihydrobenzofuranyl), the ring system being optionally substituted with one or two substituents independently selected from fluorine, chlorine, cyano, nitro, methyl, cyanomethyl, trifluoromethyl, methoxy, trifluoromethoxy, methylthio, methylcarbonyl (acetyl), methylcarbonylamino (acetylamino), phenyl and benzyloxy.

Particular values for $G^2$ include the following:

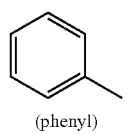
(phenyl)
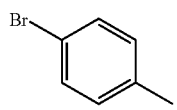
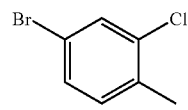

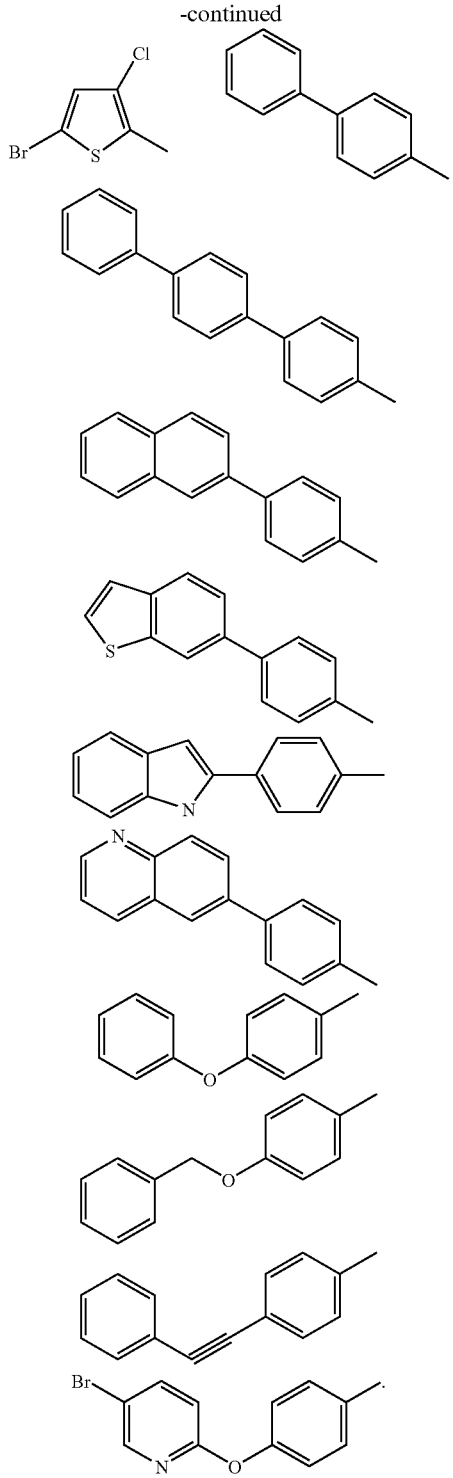

In an embodiment of the invention:
X represents —NH— or —N(CH$_3$)—;
Y represents NH;
$Z^1$ and $Z^2$ both represent an oxygen atom;
$R^1$ represents hydrogen or methyl;
$R^2$ represents hydrogen;
$R^3$ represents hydrogen;

L represents —C(O)CH₂—, —(CH₂)₂—, —CH(CH₃)—, —CH(CH₃)CH₂—, —CH(OH)—CH(CH₃)—, —CH(OH)CH₂—, —CH(OCH₃)CH₂—, —CH₂—O—(CH₂)₂, cyclopropyl, cyclopropylmethyl, or L represents a C₃ alkylene chain, the ends of which are attached to adjacent ring carbon atoms in the 5- to 9-membered ring system of G² to form a ring;

G² represents represents a saturated or unsaturated 5- to 9-membered ring system which may comprise one ring heteroatom selected from nitrogen and sulphur, the ring system being optionally substituted with one or two substituents independently selected from halogen, C₁–C₄ alkyl and a group of formula

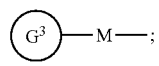

(II)

M represents a bond, —O— or —C≡C—; and

G³ represents an unsaturated 5- to 10-membered ring system which may comprise one or two ring heteroatoms independently selected from nitrogen, oxygen and sulphur, the ring system being optionally substituted with one or two substituents independently selected from fluorine, chlorine, cyano, nitro, methyl, cyanomethyl, trifluoromethyl, methoxy, trifluoromethoxy, methylthio, methylcarbonyl, methylcarbonylamino, phenyl and benzyloxy.

Examples of compounds of the invention include:

2-(2,5-Dioxoimidazolidin-4-yl)-N-[2-(4'-fluoro-biphenyl-4-yl)-ethyl]-acetamide,
N-[2-(4'-Cyano-biphenyl-4-yl)-ethyl]-2-(2,5-dioxoimidazolidin-4-yl)-acetamide,
2-(2,5-Dioxoimidazolidin-4-yl)-N-(2-phenyl-cyclopropyl)-acetamide,
N-[2-(4-Chlorophenyl)ethyl]-2-(2,5-dioxoimidazolidin-4-yl)-acetamide,
N-(2-Biphenyl-4-yl-ethyl)-2-(2,5-dioxoimidazolidin-4-yl)-acetamide,
2-(2,5-Dioxoimidazolidin-4-yl)-N-[2-(7-methyl-1H-indol-3-yl)ethyl]-acetamide,
2-(2,5-Dioxoimidazolidin-4-yl)-N-[2-(4-phenoxyphenyl)ethyl]-acetamide,
2-(2,5-Dioxoimidazolidin-4-yl)-N-[2-(4-fluorophenyl)ethyl]-acetamide,
N-[2-(4-Bromophenyl)ethyl]-2-(2,5-dioxoimidazolidin-4-yl)-acetamide,
N-[2-(2,4-Dichlorophenyl)ethyl]-2-(2,5-dioxoimidazolidin-4-yl)-acetamide,
N-[2-(3'-Chloro-biphenyl-4-yl)-ethyl]-2-(2,5-dioxoimidazolidin-4-yl)-acetamide,
N-[2-(4'-Benzyloxy-biphenyl-4-yl)-ethyl]-2-(2,5-dioxoimidazolidin-4-yl)-acetamide,
2-(2,5-Dioxoimidazolidin-4-yl)-N-[2-(4-thiophen-3-yl-phenyl)ethyl]-acetamide,
2-(2,5-Dioxoimidazolidin-4-yl)-N-[2-(4-thiophen-2-yl-phenyl)ethyl]-acetamide,
N-[2-(4'-Chloro-bipheny-4-yl)-ethyl]-2-(2,5-dioxoimidazolidin-4-yl)-acetamide,
2-(2,5-Dioxoimidazolidin-4-yl)-N-[2-(4'-methylsulfanyl-biphenyl-4-yl)ethyl]-acetamide,
2-(2,5-Dioxoimidazolidin-4-yl)-N-[2-(3'-nitro-biphenyl-4-yl)ethyl]-acetamide,
2-(2,5-Dioxoimidazolidin-4-yl)-N-[2-(4'-methyl-biphenyl-4-yl)ethyl]-acetamide,
N-[2-(3'-Acetylamino-biphenyl-4-yl)ethyl]-2-(2,5-dioxoimidazolidin-4-yl)-acetamide,
2-(2,5-Dioxoimidazolidin-4-yl)-N-[2-(4-naphthalen-2-yl-phenyl)ethyl]-acetamide,
N-[2-(3',5'-Dichloro-biphenyl-4-yl)ethyl]-2-(2,5-dioxoimidazolidin-4-yl)-acetamide,
2-(2,5-Dioxoimidazolidin-4-yl)-N-[2-(3'-methyl-biphenyl-4-yl)ethyl]-acetamide,
N-[2-(4-Benzofuran-2-yl-phenyl)ethyl]-2-2,5-dioxoimidazolidin-4-yl)-acetamide,
2-(2,5-Dioxoimidazolidin-4-yl)-N-[2-(3'-methoxy-biphenyl-4-yl)ethyl]-acetamide,
2-(2,5-Dioxoimidazolidin-4-yl)-N-(2-[1,1';4',1"]terphenyl-4-ylethyl)-acetamide,
N-[2-(4'-Acetyl-biphen-yl4-yl)ethyl]-2-(2,5dioxoimidazolidin-4-yl)-acetamide,
N-[2-(4-Benzo[b]thiophen-2-yl-phenyl)ethyl]-2-(2,5-dioxoimidazolidin-4-yl)-acetamide,
N-[2-(4'-Cyanomethyl-biphenyl-4-yl)ethyl]-2-(2,5-dioxoimidazolidin-4-yl)-acetamide,
2-(2,5-Dioxoimidazolidin-4-yl)-N-[2-(4-pyridin-3-yl-phenyl)ethyl]-acetamide,
2-(2,5-Dioxoimidazolidin-4-yl)-N-{2-[4-(1H-pyrrol-2-yl)phenyl]ethyl}-acetamide,
2-(2,5-Dioxoimidazolidin-4-yl)-N-[2-(4-furan-3-yl-phenyl)ethyl]-acetamide,
2-(2,5-Dioxoimidazolidin-4-yl)-N-[2-(4-furan-2-yl-phenyl)ethyl]-acetamide,
2-(2,5-Dioxoimidazolidin-4-yl)-N-(2-thiophen-2-yl-ethyl)-acetamide,
N-[2-(4-tert-Butylphenyl)ethyl]-2-(2,5-dioxoimidazolidin-4-yl)-acetamide,
N-[2-(4-Chlorophenyl)-1-methylethyl]-2-(2,5-dioxoimidazolidin-4-yl)acetamide,
N-{[1-(4-Chlorophenyl)cyclopropyl]methyl}-2-(2,5-dioxoimidazolidin-4-yl)acetamide,
N-2,3-Dihydro-1H-inden-2-yl-2-(2,5-dioxoimidazolidin-4-yl)acetamide,
N-[2-(4-Chlorophenyl)ethyl]-2-(4-methyl-2,5-dioxoimidazolidin-4-yl)acetamide,
N-[2-(4-Chlorophenyl)propyl]-2-(4-methyl-2,5-dioxoimidazolidin-4-yl)acetamide,
N-[2-(4'-Cyano-1,1'-biphenyl-4-yl)ethyl]-2-(4-methyl-2,5-dioxoimidazolidin-4-yl)acetamide,
N-[2-(4'-Fluoro-1,1'-biphenyl-4-yl)ethyl]-2-(methyl-2,5-dioxoimidazolidin-4-yl)acetamide,
2-(2,5-Dioxoimidazolidin-4-yl)-N-[2-(4'-fluoro-1,1'-biphenyl-4-yl)propyl]-acetamide,
N-[(1S,2R)-2-(4'-Methoxybiphenyl-4-yl)cyclopropyl]-2-(4-methyl-2,5-dioxoimidazolidin-4-yl)-acetamide,
N-[(1S,2R)-2-(4'-Cyanobiphenyl-4-yl)cyclopropyl]-2-(4-methyl-2,5-dioxoimidazolidin-4-yl)-acetamide,
N-[(1S,2R)-2-(4'-Acetylbiphenyl-4-yl)cyclopropyl]-2-(4-methyl-2,5-dioxoimidazolidin-4-yl)-acetamide,
N-{(1S,2R)-2-[4'-(Acetylamino)biphenyl-4-yl]cyclopropyl}-2-(4-methyl-2,5-dioxoimidazolidin-4-yl)-acetamide,
N-[2-(4'-Cyanobiphenyl-4-yl)propyl]-2-(4methyl-2,5-dioxoimidazolidin-4-yl)-acetamide,
2-(2,5-Dioxoimidazolidin-4-yl)-N-[2-3'-methoxybiphenyl-4-yl)ethyl]-acetamide,
N-[2-(4'-Cyano-3'-methylbiphenyl-4-yl)propyl]-2-(4-methyl-2,5-dioxoimidazolidin-4-yl)-acetamide,
2-(2,5-Dioxoimidazolidin-4-yl)-N-methyl-N-(2-phenyl-ethyl)-acetamide,
N-[1-(4-Chlorophenyl)ethyl]-2-(2,5-dioxoimidazolidin-4-yl)-acetamide, 2-(2,5-Dioxoimidazolidin-4-yl)-N-(2-hydroxy-1-methyl-2-phenylethyl)-acetamide,
N-{2-[4-(1,3-Benzodioxol-5-yl)phenyl]propyl}-2-(2,5-dioxoimidazolidin-4-yl)-acetamide,
2-(2,5-Dioxoimidazolidin-4-yl)-N-[2-(3'-methoxybiphenyl-4-yl)propyl]-acetamide,
N-{2-[3'-(Acetylamino)biphenyl-4-yl]propyl}-2-(2,5-dioxoimidazolidin-4-yl)-acetamide,
N-[2-(3'-Acetylbiphenyl-4-yl)propyl]-2-(2,5-dioxoimidazolidin-4-yl)-acetamide,
N-[2-(4'-Acetylbiphenyl-4-yl)propyl]-2-(2,5-dioxoimidazolidin-4-yl)-acetamide,
N-{2-[4-(1-Benzothien-2-yl)phenyl]propyl}-2-(2,5-dioxoimidazolidin-4-yl)-acetamide,
N-[2-(3'-Cyanobiphenyl-4-yl)propyl]-2-(2,5-dioxoimidazolidin-4-yl)-acetamide,
N-[2-(4'-Cyanobiphenyl-4-yl)propyl]-2-(2,5-dioxoimidazolidin-4-yl)-acetamide,
2-(2,5-Dioxoimidazolidin-4-yl)-N-[2-(4'-fluoro-3'-methylbiphenyl-4-yl)propyl]-acetamide,
2-(2,5-Dioxoimidazolidin-4-yl)-N-{2-[3'-(methylthio)biphenyl-4-yl]propyl}-acetamide,
2-(2,5-Dioxoimidazolidin-4-yl)-N-{2-[4-(6-methoxypyridin-3-yl)phenyl]propyl}-acetamide,
2-(2,5-Dioxoimidazolidin-4-yl)-N-[2-(4'-methoxy-3'-methylbiphenyl-4-yl)propyl]-acetamide,
N-{2-[4-(2,3-Dihydro-1-benzofuran-5-yl)phenyl]propyl}-2-(2,5-dioxoimidazolidin-4-yl)-acetamide,
2-(2,5-Dioxoimidazolidin-4-yl)-N-{2-[3'-(trifluoromethoxy)biphenyl-4-yl]propyl}-acetamide,
N-[2-(3',4'-Dimethoxybiphenyl-4-yl)propyl]-2-(2,5-dioxoimidazolidin-4-yl)-acetamide,
2-(2,5-Dioxoimidazolidin-4-yl)-N-[2-(4-quinolin-3-ylphenyl)propyl]-acetamide,
N-[2-(4'-Cyano-3'-methylbiphenyl-4-yl)propyl]-2-(2,5-dioxoimidazolidin-4-yl)-acetamide,
N-[5-(1,3-Benzodioxol-5-yl)-2,3-dihydro-1H-inden-2-yl]-2-(2,5-dioxoimidazolidin-4-yl)-acetamide,
2-(2,5-Dioxoimidazolidin-4-yl)-N-[5-(3-methoxyphenyl)-2,3-dihydro-1H-inden-2-yl]-acetamide,
N-{5-[3-(Acetylamino)phenyl]-2,3-dihydro-1H-inden-2-yl}-2-(2,5-dioxoimidazolidin-4-yl)-acetamide,
N-[5-(3-Acetylphenyl)-2,3-dihydro-1H-inden-2-yl]-2-(2,5-dioxoimidazolidin-4-yl)-acetamide,
N-[5-(4-Acetylphenyl)-2,3-dihydro-1H-inden-2-yl]-2-(2,5-dioxoimidazolidin-4-yl)-acetamide,
N-[5-(1-Benzothien-2-yl)-2,3-dihydro-1H-inden-2-yl]-2-(2,5-dioxoimidazolidin-4-yl)-acetamide,
N-[5-(3-Cyanophenyl)-2,3-dihydro-1H-inden-2-yl]-2-(2,5-dioxoimidazolidin-4-yl)-acetamide,
N-5-(4-Cyanophenyl)-2,3-dihydro-1H-inden-2-yl]-2-(2,5-dioxoimidazolidin-4-yl)-acetamide,
2-(2,5-Dioxoimidazolidin-4-yl)-N-[5-(4-fluoro-3-methylphenyl)-2,3-dihydro-1H-inden-2-yl]-acetamide,
2-(2,5-Dioxoimidazolidin-4-yl)-N-{5-[3-(methylthio)phenyl]-2,3-dihydro-1H-inden-2-yl}-acetamide,
2-(2,5-Dioxoimidazolidin-4-yl)-N-[5-(6-methoxypyridin-3-yl)-2,3-dihydro-1H-inden-2-yl]-acetamide,
2-(2,5-Dioxoimidazolidin-4-yl)-N-[5-(4-methoxy-3-methylphenyl)-2,3-dihydro-1H-inden-2-yl]-acetamide,
N-[5-(2,3-Dihydro-1-benzofuran-5-yl)-2,3-dihydro-1H-inden-2-yl]-2-(2,5-dioxoimidazolin-4-yl)acetamide,
N-[5-(3,4-Dimethoxyphenyl)-2,3-dihydro-1H-inden-2-yl]-2-(2,5-dioxoimidazolidin-4-yl)-acetamide,
N-[2-(4'-Fluorobiphenyl-4-yl)propyl]-2-(4-methyl-2,5-dioxoimidazolidin-4-yl)-acetamide,
N-{2-[4-(1,3-Benzodioxol-5-yl)phenyl]propyl}-2-(4-methyl-2,5-dioxoimidazolidin-4-yl)-acetamide,
N-[2-(3'-Methoxybiphenyl-4-yl)propyl]-2-(4-methyl-2,5-dioxoimidazolidin-4-yl)-acetamide,
N-{2-[4-(1-Benzothien-2-yl)phenyl]propyl}-2-(4-methyl-2,5-dioxoimidazolidin-4-yl)-acetamide,
N-[2-(3'-Cyanobiphenyl-4-yl)propyl]-2-(4-methyl-2,5-dioxoimidazolidin-4-yl)-acetamide,
N-[2-(4'-Fluoro-3'-methylbiphenyl-4-yl)propyl]-2-(4-methyl-2,5-dioxoimidazolidin-4-yl)-acetamide,
2-(4-Methyl-2,5-dioxoimidazolidin-4-yl)-N-{2-[3'-(methylthio)biphenyl-4-yl]propyl}-acetamide,
N-{2-[4-(6-Methoxypyridin-3-yl)phenyl]propyl}-2-(4-methyl-2,5-dioxoimidazolidin-4-4-yl)-acetamide,
N-[2-(4'-Methoxy-3'-methylbiphenyl-4-yl)propyl]-2-(4-methyl-2,5-dioxoimidazolidin-4-yl)-acetamide,
N-{2-[4-(2,3-Dihydro-1-benzofuran-5-yl)phenyl]propyl}-2-(4-methyl-2,5-dioxoimidazolidin-4-yl)-acetamide,
2-(4-Methyl-2,5-dioxoimidazolidin-4-yl)-N-{2-[3'-(trifluoromethoxy)biphenyl-4-yl]propyl}-acetamide,
N-[2-(3',4'-Dimethoxybiphenyl-4-yl)propyl]-2-(4-methyl-2,5-dioxoimidazolidin-4-yl)-acetamide,
2-(4-Methyl-2,5-dioxoimidazolidin-4-yl)-N-[2-(4-quinolin-3-ylphenyl)propyl]-acetamide,
N-[5-(4-Fluorophenyl)-2,3dihydro-1H-inden-2-yl]-2-(4methyl-2,5-dioxoimidazolidin-4-yl)-acetamide,
N-[5-(1,3-Benzodioxol-5-yl)-2,3-dihydro-1H-inden-2-yl]-2-(4-methyl-2,5-dioxoimidazolidin-4-yl)-acetamide,
N-[5-(3-Methoxyphenyl)-2,3-dihydro-1H-inden-2-yl]-2-(4-methyl-2,5-dioxoimidazolidin-4-yl)-acetamide,
N-{5-[3-(Acetylamino)phenyl]-2,3-dihydro-1H-inden-2-yl}-2-(4-methyl-2,5-dioxoimidazolidin-4-yl)-acetamide,
N-[5-(3-Acetylphenyl)-2,3-dihydro-1H-inden-2-yl]-2-(4methyl-2,5-dioxoimidazolidin-4-yl)-acetamide,
N-[5-(4-Acetylphenyl)-2,3-dihydro-1H-inden-2-yl]-2-(4-methyl-2,5-dioxoimidazolidin-4-yl)-acetamide,
N-[5-(1-Benzothien-2-yl)-2,3-dihydro-1H-inden-2-yl]-2-(4-methyl-2,5-dioxoimidazolidin-4-yl)-acetamide,
N-[5-(3-Cyanophenyl)-2,3-dihydro-1H-inden-2-yl]-2-(4-methyl-2,5-dioxoimidazolidin-4-yl)-acetamide,
N-[5-(4-Cyanophenyl)-2,3-dihydro-1H-inden-2-yl]-2-(4-methyl-2,5-dioxoimidazolidin-4-yl)-acetamide,
N-[5-(4-Fluoro-3-methylphenyl)-2,3-dihydro-1H-inden-2-yl]-2-(4-methyl-2,5-dioxoimidazolidin-4-yl)-acetamide,
2-(4-Methyl-2,5-dioxoimidazolidin-4-yl)-N-{5-[3-(methylthio)phenyl]-2,3-dihydro-1H-inden-2-yl}-acetamide,
N-[5-(6-Methoxypyridin-3-yl)-2,3-dihydro-1H-inden-2-yl]-2-(4-methyl-2,5-dioxoimidazolidin-4-yl)-acetamide,
N-[5-(4-Methoxy-3-methylphenyl)-2,3-dihydro-1H-inden-2-yl]-2-(4-methyl-2,5-dioxoimidazolidin-4-yl)-acetamide,
N-[5-(2,3-Dihydro-1-benzofuran-5-yl)-2,3-dihydro-1H-inden-2-yl]-2-(4-methyl-2,5-dioxoimidazolidin-4-yl)-acetamide,
2-(4-Methyl-2,5-dioxoimidazolidin-4-yl)-N-{5-[3-(trifluoromethoxy)phenyl]-2,3-dihydro-1H-inden-2-yl}-acetamide,
N-[5-(3,4-Dimethoxyphenyl)-2,3-dihydro-1H-inden-2-yl]-2-(4-methyl-2,5-dioxoimidazolidin-4-yl)-acetamide,
N-[5-(4-Cyano-3-methylphenyl)-2,3-dihydro-1H-inden-2-yl]-2-(4-methyl-2,5-dioxoimidazolidin-4-yl)-acetamide,
2-(2,5-Dioxoimidazolidin-4-yl)-N-(2-{4-[4-(trifluoromethyl)phenoxy]phenyl}ethyl)-acetamide,
2-(2,5-Dioxoimidazolidin-4-yl)-N-{2-[4-(4-methoxyphenoxy)phenyl]ethyl}-acetamide,
2-(2,5-Dioxoimidazolidin-4-yl)-N-(2-{4-[4-(trifluoromethoxy)phenoxy]phenyl}ethyl)-acetamide, N-{2-[4-(4–Chlorophenoxy)phenyl]ethyl}-2-(2,5-dioxoimidazolidin-4-yl)-acetamide,
N-{2-[4-(4-Acetylphenoxy)phenyl]ethyl}-2-(2,5-dioxoimidazolidin-4-yl)-acetamide,
2-(2,5-Dioxoimidazolidin-4-yl)-N-{2-[4-(pyridin-3-yloxy)phenyl]ethyl}-acetamide,
2-(2,5-Dioxoimidazolidin-4-yl)-N-(2-{4-[(6-methoxypyridin-3-yl)oxy]phenyl}ethyl)-acetamide,
N-{2-[4-(4-Cyanophenoxy)phenyl]ethyl }-2-(2,5-dioxoimidazolidin-4-yl)-acetamide,
2-(2,5-Dioxoimidazolidin-4-yl)-N-{2-[4-(4-methylphenoxy)phenyl]ethyl}-acetamide,
2-(2,5-Dioxoimidazolidin-4-yl)-N-{2-[4-(4-fluorophenoxy)phenyl]ethyl}-acetamide,
N-(2-Biphenyl-4yl-2-hydroxy-ethyl)-2-(2,5-dioxoimidazolidin-4-yl)-acetamide,
N-[2-(1,1'-Biphenyl-4-yl)-2-methoxyethyl]-2-(2,5-dioxoimidazolidin-4-yl)-acetamide,
N-[2-(1,1'-Biphenyl-4-yl)-ethyl]-2-(2,5-dioxoimidazolidin-4-yl)-N-methylacetamide,
2-(2,5-Dioxoimidazolidin-4-yl)-N-[2-(4-phenylethynyl-piperidin-1-yl)ethyl]-acetamide,
N-{2-[(4-Bromobenzyl)oxy]ethyl}-2-(2,5-dioxoimidazolidin-4-yl)-acetamide,
2-(1,1'-Biphenyl-4-yl)-2-oxoethyl (2,5-dioxoimidazolidin-4-yl)acetate, and pharmaceutically acceptable salts and solvates thereof.

It will be appreciated that the particular substituents and number of substituents in the compounds of the invention are selected so as to avoid sterically undesirable combinations.

Each exemplified compound represents a particular and independent aspect of the invention.

It will be appreciated that the compounds according to the invention may contain one or more asymmetrically substituted carbon atoms. The presence of one or more of these asymmetric centres (chiral centres) in compounds according to the invention can give rise to stereoisomers, and in each case the invention is to be understood to extend to all such stereoisomers, including enantiomers and diastereomers, and mixtures including racemic mixtures thereof. Racemates may be separated into individual optically active forms using known procedures (cf. Advanced Organic Chemistry: 3rd Edition: author J March, p 104–107) including for example the formation of diastereomeric derivatives having convenient optically active auxiliary species followed by separation and then cleavage of the auxiliary species.

Where optically active centres exist in the compounds of the invention, we disclose all individual optically active forms and combinations of these as individual specific embodiments of the invention, as well as their corresponding racemates.

Where tautomers exist in the compounds of the invention, we disclose all individual tautomeric forms and combinations of these as individual specific embodiments of the invention.

The compounds of the invention may be provided as pharmaceutically acceptable salts or solvates. These include acid addition salts such as hydrochloride, hydrobromide, citrate, tosylate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine. Examples of solvates include hydrates.

The compounds of formula (I) have activity as pharmaceuticals. As previously outlined the compounds of the invention are metalloproteinase inhibitors, in particular they are inhibitors of MMP12 and may be used in the treatment of diseases or conditions mediated by MMP12 such as asthma, rhinitis, chronic obstructive pulmonary diseases (COPD), arthritis (such as rheumatoid arthritis and osteoarthritis), atherosclerosis and restenosis, cancer, invasion and metastasis, diseases involving tissue destruction, loosening of hip joint replacements, periodontal disease, fibrotic disease, infarction and heart disease, liver and renal fibrosis, endometriosis, diseases related to the weakening of the extracellular matrix, heart failure, aortic aneurysms, CNS related diseases such as Alzheimer's disease and Multiple Sclerosis (MS), and hematological disorders.

The compounds of the invention show a favourable selectivity profile. Whilst we do not wish to be bound by theoretical considerations, the compounds of the invention are believed to show selective inhibition for any one of the above indications relative to any MMP1 inhibitory activity, by way of non-limiting example they may show 100–1000 fold selectivity over any MMP1 inhibitory activity.

Accordingly, the present invention provides a compound of formula (I), or a pharmaceutically acceptable salt or solvate thereof, as hereinbefore defined for use in therapy.

In another aspect, the invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention further provides a method of treating a disease or condition mediated by MMP12 which comprises administering to a patient a therapeutically effective amount of a compound of formula (I) or a pharmaceutically acceptable salt or solvate thereof as hereinbefore defined.

The invention also provides a method of treating an obstructive airways disease (e.g. asthma or COPD) which comprises administering to a patient a therapeutically effective amount of a compound of formula (I) or a pharmaceutically acceptable salt or solvate thereof as hereinbefore defined.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 0.001 mg/kg to 75 mg/kg, in particular from 0.5 mg/kg to 30 mg/kg. This daily dose may be given in divided doses as necessary. Typically unit dosage forms w contain about 1 mg to 500 mg of a compound of this invention.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Thus, the present invention also provides a pharmaceutical composition comprising a compound of formula (I) or a pharmaceutically acceptable salt or solvate thereof as hereinbefore defined in association with a pharmaceutically acceptable adjuvant, diluent or carrier.

The invention further provides a process for the preparation of a pharmaceutical composition of the invention which comprises mixing a compound of formula (I) or a pharmaceutically acceptable salt or solvate thereof as hereinbefore defined with a pharmaceutically acceptable adjuvant, diluent or carrier.

The pharmaceutical compositions of this invention may be administered in standard manner for the disease or condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more diseases or conditions referred to hereinabove such as "Symbicort" (trade mark) product.

Preparation of the Compounds of the Invention

The present invention further provides a process for the preparation of a compound of formula (I) or a pharmaceutically acceptable salt or solvate thereof as defined above which comprises, (a) when X represents an oxygen atom or a group $NR^4$, reacting a compound of formula

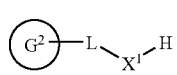

(III)

wherein $X^1$ represents an oxygen atom or a group $NR^4$ and L, $G^2$ and $R^4$ are as defined in formula (I), with an activated carboxylic acid of formula

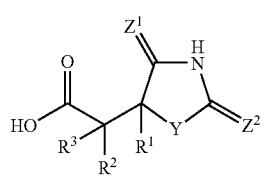

(IV)

wherein Y, $Z^1$, $Z^2$, $R^1$, $R^2$, and $R^3$ are as defined in formula (I); or (b) when X represents $CH_2$, reacting an activated carboxylic acid of formula (IV) as defined in (a) above with methoxymethylamine or a salt thereof (e.g. hydrochloride salt) followed by reaction with a Grignard reagent of formula

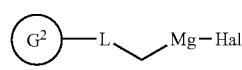

(V)

wherein Hal represents a halogen atom such as chlorine or bromine and L and $G^2$ are as defined in formula (I); or (c) when X represents $CH_2$, reacting a compound of formula

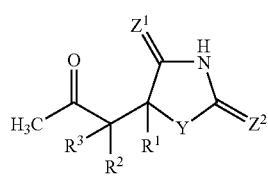

(VI)

wherein Y, $Z^1$, $Z^2$, $R^1$, $R^2$ and $R^3$ are as defined in formula (C), with a compound of formula

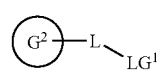

(VII)

wherein $LG^1$ represents a leaving group such as halogen or sulphonate (e.g. methylsulphonate or toluenesulphonate) and L and $G^2$ are as defined in formula (I), in the presence of a strong base (e.g. sodium hydride or lithium diisopropylamide);

and optionally after (a), (b) or (c) forming a pharmaceutically acceptable salt or solvate.

In process (a), the reaction between the compounds of formulae (m) and (IV) represents a simple amide or ester coupling well known to those skilled in the art. The carboxylic acid of formula (IV) must be activated in some way, for example as the acid halide, anhydride, acyl urea or acyl derivative of N-hydroxysuccinimide. For a general description of the preparation of amides and esters see, for example, Carey, F. A. and Sundberg, J., Advanced Organic Chemistry, 3rd Edition, pp 144–152, 1990.

It will be appreciated by those skilled in the art that in the processes of the present invention certain functional groups such as hydroxyl or amino groups in the starting reagents or intermediate compounds may need to be protected by protecting groups. Thus, the preparation of the compounds of the invention may involve, at various stages, the addition and removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3rd edition, T. W. Greene and P. G. M. Wuts, Wiley-Interscience (1999).

Compounds of formulae (III), (IV), (V), (VI) and (VII) are either commercially available, are known in the literature or may be prepared using known techniques.

For example, compounds of formula (IV) in which $R^1$ represents a hydrogen atom, Y represents NH and $Z^1$ and $Z^2$ both represent oxygen may be prepared accoding to the reaction scheme below:

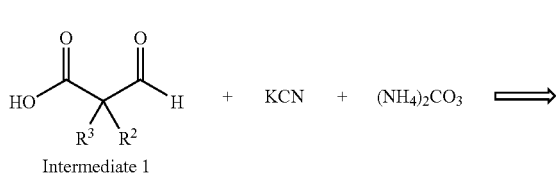

Intermediate 1

-continued

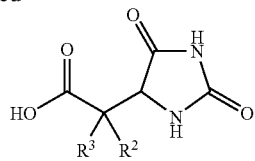

Alternatively, compounds of formula (IV) in which $R^1$ represents a hydrogen atom, Y represents NH, $Z^1$ represents sulphur and $Z^2$ represent oxygen may be prepared by reacting Intermediate 1 above with thiocarbamic acid ($H_2N$—C(S)—OH) and sodium cyanide in the presence of a solvent mixture of ethanol and water, e.g. as described in *J. Chem. Soc.*, 1959, page 396.

Other methods are available for preparing compounds of formula (IV). For example, a wide range of α-amino acids are useful as synthons to dioxo-imidazolidines and oxo-thioxo-imidazolidines. It is well known that salts of cyanic acid, urea, or thiocyanic acid together with an ammonium salt react with α-amino acids to form these heterocycles (Anteunis, M. J. O.; Spiessens, L.; Witte, M. De; Callens, R.; Reyniers, *Bull. Soc. Chim. Belg.*, EN, 96, 6, 1987, 459–466; Dakin; *Am. Chem. J.*, 44, 1910, 49; Haurowitz et al., *J. Biol. Chem.*, 224, 1957).

Several suitable dioxo-imidazolidine and oxo-thioxo-imidazolidine acids are commercially available or are described in the literature as indicated below (unless otherwise stated, the numbers in brackets are CAS registry numbers):
(2,5-Dioxo-imidazolidin-4-yl)-acetic acid (5427-26-9, 26184-52-1, 26184-53-2, 67337-71-7);
(3-Methyl-2,5-dioxo-imidazolidin-4-yl)-acetic acid (26972-46-3);
5-Oxo-2-thioxo-imidazolidin-4-yl)-acetic acid (41679-36-1, 61160-00-7);
(2,5-Dioxo-4-phenyl-imidazolidin-4-yl)-acetic acid (62985-01-7);
(4-Methyl-2,5-dioxo-imidazolidin-4yl)-acetic acid (beilstein registry number 145446);
4-Imidazolidineacetic acid, 4-(hydroxymethyl)-2,5-dioxo-, (4R)- (9CI) (391870-39-6);
4-Imidazolidineacetic acid, 4-(4-chlorophenyl)-2,5-dioxo- (9CI) (250352-11-5);
4-Imidazolidineacetic acid, α-methyl-2,5-dioxo- (9CI) (184681-52-5);
1,3-Diazaspiro[4.4]nonane-6-carboxylic acid, 2,4-dioxo-, cis- (9CI) (147676-21-9);
1,3-Diazaspiro[4.5]decane-6-carboxylic acid, 2,4-dioxo- (7CI, 8CI) (947-104);
1,3-Diazaspiro[4.4]nonane-6-carboxylic acid, 2-oxo-4-thioxo- (9CI) (197315-95-0);
4-Imidazolidineacetic acid, 5-oxo-2-thioxo- (9CI) (41679-36-1);
4,4-Imidazolidinediacetic acid, 2,5-dioxo- (8CI, 9CI) (5624-17-9); and
4-Imidazolidineacetic acid, 4-hydroxy-2,5-dioxo- (9CI) (78703-76-1).

The present invention will now be further explained by reference to the following illustrative examples.

General Procedures $^1$HNMR and $^{13}$CNMR were recorded on a Varian$^{unity}$ Inova 400 MHz or a Varian Mercury-VX 300 MHz instrument. The central peaks of chloroform-d ($\delta_H$ 7.27 ppm), dimethylsulfoxide-d$_6$ ($\delta_H$ 2.50 ppm) or methanol-d$_4$ ($\delta_H$ 3.31 ppm) where used as internal references. Low-resolution mass spectra were obtained on an Agilent 100 LC-MS system equipped with an APCI ionisation chamber. Column chromatography was carried out using silica gel (0.063–0.2 mm) (Merck). Unless stated otherwise, starting materials were commercially available. All solvents and commercial reagents were laboratory grade and used as received.

| Abbreviations: | |
|---|---|
| NMP: | 1-methyl-2-pyrollidinone |
| TFA: | trifluoroacetic acid |
| HOBT: | 1-hydroxybenzotriazole |
| PdCl$_2$ (dppf): | bis(diphenylphosphino)ferrocene-palladium(II)chloride dichloromethane complex |
| THF: | tetrahydrofuran |
| BOC: | tert-butoxycarbonyl |
| EtOH: | ethanol |
| EtOAc: | ethyl acetate |
| TLC: | thin layer chromatography |
| DMSO: | dimethyl sulphoxide |
| PEG: | polyethylene glycol |

EXAMPLES

A. General Procedure for Preparation of 2-(2.5-Dioxo-imidazolidin-4-yl)-acetamides I. Preparation of Non-commercial Amines

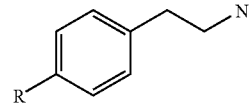

2-(4-Bromo-phenyl)-ethylamine (2 mmol, 400 mg) was dissolved in 4 mL THF (dry, mol sieves) and di-tert-butyl dicarbonate (1.2 eq 2.4 mmol 520 mg) was added slowly. The reaction mixture was stirred in room temperature for 1 hour before it was diluted with 100 mL ethyl acetate and washed with 100 mL sat. NaHCO$_3$/aq. The organic phase was dried over Na$_2$SO$_4$, filtrated and evaporated to dryness. The BOC-protected amine was dissolved in a mixture of 10 mL toluene, 2.5 mL ethanol and 2.5 mL 2M Na$_2$CO$_3$/aq. PdCl$_2$(dppf) (0.03 eq, 50 mg) was added together with a corresponding boronic acid (1.05 eq, 2.1 mmol). The solution was degassed with nitrogen and the vessel was sealed before it was stirred overnight at 80° C. The reaction mixture was diluted with 50 mL toluene and 50 mL water. After mixing, the organic layer was transferred directly on to a silica column and purified by chromatography (toluene-ethylacetate). To remove the protecting group the compound was stirred in a mixture of 5 mL conc. HCl in 10 mL THF for 30 min. The solution was neutralised with 1M NaOH/aq and extracted with dichloromethane (2×). The combined organic layers was dried over Na$_2$SO$_4$, filtrated and evaporated to dryness. The amines were used in the amide synthesis without any further purification.

II. Coupling of Amines to 5 Hydantoin Acetic Acid:—Amide Synthesis

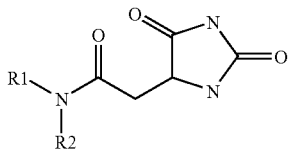

600 µL of a 0.15 solution in NMP of 5-hydantoin acetic acid was mixed with 98 mg of polystyrene-bound carbodiimide resin (loading 1.28 mmol/g). 340 µL of a 0.3M solution of HOBT in NMP was added to the mixture and vortexed for 10 minutes before 200 µL of a 0.3M solution in NMP of the corresponding amine was added. The reaction mixtures were vortexed overnight at room temperature in sealed vessels. Resin was removed by filtration and the solution was evaporated to dryness. The products were purified on semiprep-HPLC $C_{18}$-column ($H_2O:CH_3CN$, 0.1% TFA buffer, gradient 10% to 95% $CH_3CN$, 10 min).

The following 2-(2,5-Dioxo-imidazolidin-4-yl)-acetamides were prepared according to the general procedure A outlined above.

Example 1

2-(2,5-Dioxoimidazolidin-4-yl)-N-[2-(4'-fluoro-biphenyl-4-yl)-ethyl]-acetamide $^1$H NMR (400 MHz, DMSO-$d_6$): δ 10.56 (1H, s); 8.07 (1H, t); 7.71–7.65 (2H, m); 7.59–7.55 (2H, m); 7.32–7.24 (4H, m); 4.23–4.19 (1H, m); 3.35–3.26 (2H, m); 2.75 (2H, t) 2.56–2.37(2H, m)

APCI-MS m/z: 356.4 [MH$^+$]

Example 2

N-[2-(4'-Cyano-biphenyl-4-yl)-ethyl]-2-(2,5-dioxoimidazolidin-4-yl)-acetamide $^1$H NMR (400 MHz, DMSO-$d_6$): δ 10.56 (1H, s); 8.07 (1H, t); 7.92–7.84 (4H, m); 7.79 (1H, s); 7.69 (2H, d); 7.35 (2H, d); 4.21(1H, t); 3.37–3.27 (2H, m); 2.78 (2H, t) 2.57–2.36(2H, m)

APCI-MS m/z: 363.4 [MH$^+$]

Example 3

2-(2,5-Dioxoimidazolidin-4-yl)-N-(2-phenyl-cyclopropyl)-acetamide

APCI-MS m/z: 274.3 [MH$^+$]

Example 4

N-[2-(4-Chlorophenyl)ethyl]-2-(2,5-dioxoimidazolidin-4-yl)-acetamide

APCI-MS m/z: 296.3 [MH$^+$]

Example 5

N-(2-Biphenyl-4-yl-ethyl)-2-(2,5-dioxoimidazolidin-4-yl)-acetamide

APCI-MS m/z: 338.4 [MH$^+$]

Example 6

2-(2,5-Dioxoimidazolidin-4-yl)-N-[2-(7-methyl-1H-indol-3-yl)ethyl]acetamide

APCI-MS m/z: 315.3 [MH$^+$]

EXAMPLE 7

2-(2,5-Dioxoimidazolidin-4-yl)-N-[2-(4-phenoxyphenyl)ethyl]-acetamide

APCI-MS m/z: 354.4 [MH$^+$]

Example 8

2-(2,5-Dioxoimidazolidin-4-yl)-N-[2-(4-fluorophenyl)ethyl]-acetamide

APCI-MS m/z: 280.3 [MH$^+$]

Example 9

N-[2-(4-Bromophenyl)ethyl]-2-(2,5-dioxoimidazolidin-4-yl)-acetamide

APCI-MS m/z: 340.3; 342.3 [MH$^+$]

Example 10

N-[2-(2,4-Dichlorophenyl)ethyl]-2-(2,5-dioxoimidazolidin-4-yl)-acetamide

APCI-MS m/z: 330.3; 332.3[MH$^+$]

Example 11

N-[2-(3'-Chloro-biphenyl-4-yl)-ethyl]-2-(2,5-dioxoimidazolidin-4-yl)-acetamide

APCI-MS m/z: 372.4 [MH$^+$]

Example 12

N-[2-(4'-Benzyloxy-biphenyl-4-yl)-ethyl]-2-(2,5-dioxoimidazolidin-4-yl)-acetamide APCI-MS m/z: 444.5 [MH$^+$]

Example 13

2-(2,5-Dioxoimidazolidin-4-yl)-N-[2-(4-thiophen-3-yl-phenyl)ethyl]-acetamide

APCI-MS m/z: 344.3 [MH$^+$]

Example 14

2-(2,5-Dioxoimidazolidin-4-yl)-N-[2-(4-thiophen-2-yl-phenyl)ethyl]-acetamide

APCI-MS m/z: 344.3 [MH$^+$]

Example 15

N-[2-(4'-Chloro-biphenyl-4-yl)-ethyl]-2-(2,5-dioxoimidazolidin-4-yl)-acetamide

APCI-MS m/z: 372.3 [MH$^+$]

Example 16

2-(2,5-Dioxoimidazolidin-4-yl)-N-[2-(4'-methylsulfanyl-biphenyl-4-yl)ethyl]-acetamide APCI-MS m/z: 384.4 [MH$^+$]

Example 17

2-(2,5-Dioxoimidazolidin-4-yl)-N-[2-(3'-nitro-biphenyl-4-yl)ethyl]-acetamide

APCI-MS m/z: 383.4 [MH$^+$]

Example 18

2-(2,5-Dioxoimidazolidin-4-yl)-N-[2-(4'-methyl-biphenyl-4-yl)ethyl]-acetamide

APCI-MS m/z: 352.4 [MH$^+$]

Example 19

N-[2-(3'-Acetylamino-biphenyl-4-yl)ethyl]-2-(2,5-dioxoimidazolidin-4-yl)-acetamide APCI-MS m/z: 395.4 [MH$^+$]

Example 20

2-(2,5-Dioxoimidazolidin-4-yl)-N-[2-(4-naphthalen-2-yl-phenyl)ethyl]-acetamide

APCI-MS m/z: 388.4 [MH$^+$]

Example 21

N-[2-(3',5'-Dichloro-biphenyl-4-yl)ethyl]-2-(2,5-dioxoimidazolidin-4-yl)-acetamide APCI-MS m/z: 406.3; 408.4 [MH$^+$]

Example 22

2-(2,5-Dioxoimidazolidin-4-yl)-N-[2-(3'-methyl-biphenyl-4-yl)ethyl]-acetamide

APCI-MS m/z: 352.4 [MH$^+$]

Example 23

N-[2-(4-Benzofuran-2-yl-phenyl)ethyl]-2-(2,5dioxoimidazolidin-4-yl)-acetamide

APCI-MS m/z: 378.4 [MH$^+$]

Example 24

2-(2,5-Dioxoimidazolidin-4-yl)-N-[2-(3'-methoxy-biphenyl-4-yl)ethyl]-acetamide

APCI-MS m/z: 368.3 [MH$^+$]

Example 25

2-(2,5-Dioxoimidazolidin-4-yl)-N-(2-[1,1';4',1"]terphenyl-4-ylethyl)-acetamide

APCI-MS m/z: 414.4 [MH$^+$]

Example 26

N-[2-(4'-Acetyl-biphenyl-4-yl)ethyl]-2-(2,5-dioxoimidazolidin-4-yl)-acetamide

APCI-MS m/z: 380.4 [MH$^+$]

Example 27

N-[2-(4-Benzo[b]thiophen-2-yl-phenyl)ethyl]-2-(2,5-dioxoimidazolidin-4-yl)-acetamide APCI-MS m/z: 394.4 [MH$^+$]

Example 28

N-[2-(4'-Cyanomethyl-biphenyl-4-yl)ethyl]-2-(2,5-dioxoimidazolidin-4-yl)-acetamide APCI-MS m/z: 377.4 [MH$^+$]

Example 29

2-(2,5-Dioxoimidazolidin-4-yl)-N-[2-(4-pyridin-3-yl-phenyl)ethyl]-acetamide

APCI-MS m/z: 339.4 [MH$^+$]

Example 30

2-(2,5-Dioxoimidazolidin-4-yl)-N-{2-[4-(1H-pyrrol-2-yl)phenyl]ethyl}-acetamide

APCI-MS m/z: 327.4 [MH$^+$]

Example 31

2-(2,5-Dioxoimidazolidin-4-yl)-N-[2-(4-furan-3-yl-phenyl)ethyl]-acetamide

APCI-MS m/z: 328.4 [MH$^+$]

Example 32

2-(2,5-Dioxoimidazolidin-4-yl)-N-[2-(4-furan-2-yl-phenyl)ethyl]-acetamide

APCI-MS m/z: 328.4 [MH$^+$]

Example 33

2-(2,5-Dioxomidazolidin-4-yl)-N-(2-thiophen-2-yl-ethyl)-acetamide

APCI-MS m/z: 268.3 [MH+]

Example 34

N-[2-(4-tert-Butylphenyl)ethyl]-2-(2,5-dioxoimidazolidin-4-yl)-acetamide

APCI-MS m/z: 318.4 [MH+]

Example 35

N-[2-(4-Chlorophenyl)-1-methylethyl]-2-(2,5-dioxoimidazolidin-4-yl)acetamide $^1$H NMR (400 MHz,DMSO -d$_6$): δ 10.55(1H, d); 7.88 (1H, dd); 7.76 (1H, d); 7.33–7.31 (2H, m); 7.21–7.19 (2H, m); 4.19–4.16 (1H, m); 3.94–3.88 (1H, m); 2.77–2.32 (4H, m); 0.99 (3H, dd)

APCI-MS m/z: 310.3 [MH$^{30}$]

Example 36

N-{[1-(4-Chlorophenyl)cyclopropyl]methyl}-2-(2,5-dioxoimidazolidin-4-yl)acetamide $^1$H NMR (400MHz,DMSO-d$_6$): δ 10.53(1H, d); 7.95 (1H, t); 7.73 (1H, s); 7.33–7.25 (4H, m); 4.18–4.15 (1H, m); 3.39–3.22 (2H, m); 2.54–2.37 (2H, m); 0.90–0.88 (2H, m); 0.76–0.73 (2H, m)

APCI-MS m/z: 322.3 [MH+]

Example 37

N-2,3-Dihydro-1H-inden-2-yl-2-(2,5-dioxoimidazolidin-4-yl)acetamide $^1$H NMR (400 MHz,DMSO-d$_6$): δ 10.54(1H, d); 8.24 (1H, d); 7.82 (1H, s); 7.22–7.20(2H, m); 7.16–7.13 (2H, m); 4.47–4.42 (1H, m); 4.22–4.19(1H, m); 3.19–3.12(2H, m); 2.80–2.72 (2H, m); 2.54–2.36 (2H, m)

APCI-MS m/z: 274.2 [MH+]

B. General Procedure for Preparation of (4-methyl-2,5-dioxoimidazolidin-4-yl)-acetamides I. tert-butyl(4-methyl-2,5-dioxoimidazolidin-4-yl)acetate

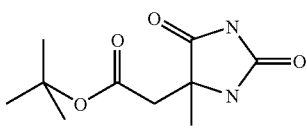

Tert-butyl acetoacetate (200 mg; 1.3 mmol), KCN (165 mg; 2.5 mmol) and (NH$_4$)$_2$CO$_3$ (605 mg; 6.3 mmol) was suspended in EtOH (2 mL) and H$_2$O (2 mL) in a sealed tube. The mixture was heated to 85–90° C. and a solution was obtained, the heating was continued over night. The resulting slightly yellow solution was allowed to cool to roomtemperature and a precipitate was formed. The mixture was neutralised with 5% NaHSO$_4$ (aq) and diluted with H$_2$O (30 mL). The slurry was extracted with EtOAc (2×50 mL). The organic phase was dried (Na$_2$SO$_4$), filtered and evaporated to give the title compound as a colourless solid. Obtained 210 mg (73% yield).

$^1$H-NMR(DMSO-D6):δ 10.58 (1H, s), 7.91 (1H, s), 2.76+ 2.39 (1H each, ABq), 1.35 (9H, s), 1.23 (3H, s) ppm.

II. (4-methyl-2,5-dioxoimidazolidin-4-yl)-acetic acid

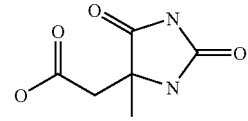

Deprotection afforded the title compound.

The following (4-methyl-2,5-dioxoimidazolidin-4-yl)acetamides were prepared by coupling of the appropiate amine to (4-methyl-2,5doxoimdazolidin-4-yl)-acetic acid by the general procedure A above.

Example 38

N-[2-(4-Chlorophenyl)ethyl]-2-(4-methyl-2,5-dioxoimidazolidin-4-yl)acetamide $^1$H NMR (400 MHz,DMSO-d$_6$): δ 10.42(1H, s); 7.94(1H, t); 7.35(1H, s); 7.35–7.31 (2H, m); 7.24–7.21 (2H, m) ; 3.21 (2H, q); 2,67 (2H, dd); 2.53–2.36 (2H, m); 1.21 (3H, s)

APCI-MS m/z: 310.3 [MH+]

Example 39

N-[2-(4-Chlorophenyl)propyl]-2-(4-methyl-2,5-dioxoimidazolidin-4-yl)acetamide $^1$H NMR (400 MHz,DMSO-d$_6$): δ 10.42 (1H,m); 7.89–7.86 (1H, m); 7.65–7.64 (1H, m); 7.35–7.32 (2H, m); 7.24–7.22 (2H, m); 3.19–3.09 (2H, m); 2.87–2.77 (1H, m); 2.53–2.37 (2H, m); 1.19 (3H, d); 1.14 (3H, d)

APCI-MS m/z: 324.4 [MH+]

Example 40

N-[2-(4'-Cyano-1,1'-biphenyl-4-yl)ethyl]-2-(4-methyl-2,5-dioxoimidazolidin-4-yl)acetamide APCI-MS m/z: 377.3 [MH+]

Example 41

N-[2-(4'-Fluoro-1,1'-biphenyl-4-yl)ethyl]-2-(4-methyl-2,5-dioxoimidazolidin-4-yl)acetamide $^1$H NMR (400 MHz,DMSO-d$_6$): δ 10.42 (1H,s); 7.99 (1H, t); 7.97–7.65 (3H, m); 7.56 (2H, d); 7.30–7.24 (4H, m); 3.28–3.23 (2H, m); 2.73–2.70 (2H, m); 2.54–2.39 (2H, m); 1.22 (3H, s)

APCI-MS m/z: 370.4 [MH+]

Example 42

2-(2,5-Dioxoimidazolidin-4-yl)-N-[2-(4'-fluoro-1,1'-biphenyl-4-yl)propyl]-acetamide a) 2-(4-Bromo-phenyl)-propylamine 2-Phenyl-propylamine (1 g, 7.4 mmol) was dissolved in n-hexane (30 mL) and HBr/aq (5 drops) together with ZnBr on silica (1.75 mmol/g, 1 g). Br$_2$ (14.8 mmol, 900 μL) was slowly added and the slurry was stirred over night. The slurry was diluted with ethyl acetate (300 mL) and washed with 2M Na$_2$CO$_3$ (300 mL). The organic phase was dried over Na$_2$SO$_4$, filtered and evaporated to dryness. Purification and separation of regioisomers was done on semi prep-HPLC C$_{18}$-column (H$_2$O :CH$_3$CN, 1% NH$_4$OAc buffer, gradient 10% to 60% CH$_3$CN, 30 min). Yield 23% b) [2-(4-Bromo-phenyl)-propyl]-carbamic acid tert-butyl ester 2-(4-Bromo-phenyl)-propylamine (18.7 mmol, 4g) was dissolved in 50 mL THF (dry, mol sieves) and di-tert-butyl dicarbonate (1.2eq 23 mmol 5 g) was added slowly. The reaction mixture was stirred at room temperature for 1 hour before it was diluted with 300 mL ethyl acetate and washed with 300 mL sat. NaHCO$_3$/aq. The organic phase was dried over Na$_2$SO$_4$, filtrated and evaporated to dryness.

c) [2-(4'-Fluoro-biphenyl-4-yl)-propyl]-carbamic acid tert-butyl ester

The BOC-protected amine obtained in b) above was dissolved in a mixture of 10 mL toluene, 2.5 mL ethanol and 2.5 mL 2M Na$_2$CO$_3$/aq. PdCl$_2$(dppf) (0.03 eq, 50 mg) and 4-fluorobenzeneboronic acid (1.05eq, 2.1 mmol) were added. The solution was degassed with nitrogen and the vessel was sealed before it was stirred overnight at 80° C. The reaction mixture was diluted with 50 mL toluene and 50 mL water. After mixing, the organic layer was transferred directly on to a silica column and purified by chromatography (toluene-ethyl acetate).

d) 2-(4'-Fluoro-biphenyl-4-yl)-propylamine

To remove the protecting group the compound obtained in c) above was stirred in a mixture of 5 mL conc. HCl in 10 mL THF for 30 min. The solution was neutralised with 1M NaOH/aq and extracted with dichloromethane (2×). The combined organic layers was dried over Na$_2$SO$_4$, filtrated and evaporated to dryness.

e) 2-(2,5-Dioxoimidazolidin-4-yl)-N-[2-(4'-fluoro-1,1'-biphenyl-4-yl)propyl]-acetamide 600μL of a 0.15M solution in NMP of 5-hydantoin acetic acid was mixed with 98 mg of polystyrene-bound caibodi-imide resin (loading 1.28 mmol/g). 340 μL of a 0.3M solution of HOBT in NMP was added to the mixture and vortexed for 10 minutes before 200 μL of a 0.3M solution in NMP of 2-(4'-fluoro-biphenyl-4-yl)-propylamine was added. The reaction mixture was vortexed overnight at room temperature in a sealed vessel. Resin was removed by filtration and the solution was evaporated to dryness. The product was purified on semi prep-HPLC C$_{18}$-column (H$_2$O: CH$_3$CN, 0.1% TFA buffer, gradient 10% to 95% CH$_3$CN, 10 min).

$^1$H NMR (400 MHz,DMSO-d$_6$): δ 10.55 (s, 1H), 8.00 (s, 1H), 7.76 (s, 1H), 7.68 (dd, J=8.7, 5.5 Hz, 2H), 7.57 (d, J=8.1 Hz, 2H), 7.32–7.25 (m, 4H), 4.22–4.17 (m, 1H), 3.32 (dd, J=20.7, 6.3 Hz, 2H), 2.92 (q, J=7.0 Hz, 1H), 2.57–2.35 (m, 2H), 1.21 (d, J=7.1 Hz, 3H).

APCI-MS m/z: 370.2 [MH$^+$]

The following compounds were prepared according to methods analogous to Example 42 above.

Example 43

N-[(1S,2R)-2-(4'-Methoxybiphenyl-4-yl)cyclopropyl]-2-(4-methyl-2,5-dioxoimidazolidin-4-yl)-acetamide $^1$H NMR (400 MHz,DMSO-d$_6$): δ 10.44 (d, J=7.6 Hz, 1H), 8.18 (dd, J=6.8, 4.3 Hz, 1H), 7.73 (s, 1H), 7.54 (d, J=8.9 Hz, 2H), 7.48 (d, J=8.3 Hz, 2H), 7.13 (dd, J=8.3, 2.8 Hz, 2H), 6.99 (d, J=8.9 Hz, 2H), 3.77 (s, 3H), 2.79–2.73 (m, 1H), 2.56–2.46 (m, 1H), 2.37 (d, J=15.2 Hz, 1H), 1.90 (dt, J=6.1, 3.1 Hz, 1H), 1.23 (s, 3H), 1.17–1.09 (m, 2H).

APCI-MS m/z: 394.3 [MH$^+$]

Example 44

N-[(1S,2R)-2-(4'-Cyanobiphenyl-4-yl)cyclopropyl]-2-(4-methyl-2,5-dioxoimidazolidin-4-yl)-acetamide APCI-MS m/z: 389.3 [MH$^+$]

Example 45

N-[(1S,2R)-2-(4'-Acetylbiphenyl-4-yl)cyclopropyl]-2-(4-methyl-2,5-dioxoimidazolidin-4-yl)-acetamide $^1$H NMR (400 MHz,DMSO-d$_6$): δ 10.44 (d, J=8.3 Hz, 1H), 8.20 (dd, J=7.3, 4.3 Hz, 1H), 8.00 (d, J=8.4 Hz, 2H), 7.78 (d, J=8.5 Hz, 2H), 7.73 (s, 1H), 7.63 (d, J=8.3 Hz, 2H), 7.21 (dd, J=8.3, 3.1 Hz, 2H), 2.80 (dd, J=7.4, 4.0 Hz, 1H), 2.59 (s, 3H), 2.56–2.35 (m, 2H), 1.95 (tq, J=6.2, 3.2 Hz, 1H), 1.23 (s, 3H), 1.22–1.13 (m, 2H).

APCI-MS m/z: 406.3[MH$^+$]

Example 46

N-{(1S,2R)-2-[4'-(Acetylamino)biphenyl-4-yl]cyclopropyl}-2-(4-methyl-2,5-dioxoimidazolidin-4-yl)-acetamide APCI-MS m/z: 421.3[MH$^+$]

Example 47

N-[2-(4'-Cyanobiphenyl-4-yl)propyl]-2-(4-methyl-2,5-dioxoimidazolidin-4-yl)-acetamide $^1$H NMR (400 MHz,DMSO-d$_6$): δ 10.43 (s, 1H), 7.95–7.85 (m, 5H), 7.67 (dd, J=14.2, 8.5 Hz, 3H), 7.36 (dd, J=8.3, 1.7 Hz, 2H), 1.19 (s, 3H), 1.21 (d, J=3.9 Hz, 3H), 3.20 (sextet, J=6.8 Hz, 2H), 2.94–2.87 (m, H), 2.54–2.39 (m, 2H).

APCI-MS m/z: 391.3 [MH$^+$]

Example 48

2-(2,5-Dioxoimidazoldin-4-yl)-N-[2-(3'-methoxybiphenyl-4-yl)ethyl]-acetamide $^1$H NMR (400 MHz,DMSO-d$_6$): δ 10.56 (s, 1H), 8.07 (t, J=5.5 Hz,1H), 7.80 (s, 1H), 7.59 (d, J=8.1 Hz, 2H), 7.36 (t, J=8.0Hz, 1H), 7.30 (d, J=8.2 Hz, 2H), 7.20 (d, J=7.7 Hz, 1H), 7.16 (t, J=2.0 Hz, 1H), 6.91 (dd, J=8.1, 2.3 Hz, 1H), 4.24–4.20 (m, 1H), 3.82 (s, 3H), 3.34–3.26 (m, 2H), 2.75 (t, J=7.3 Hz, 2H), 2.57–2.37 (m, 2H ).

APCI-MS m/z: 368.2[MH$^+$]

Example 49

N-[2-(4'-Cyano-3'-methylbiphenyl-4-yl)propyl]-2-(4-methyl-2,5-dioxoimidazolidin-4-yl)-acetamide $^1$H NMR (400 MHz,DMSO-d$_6$): δ 10.41 (s, 1H), 7.92 (t, J=5.6Hz, 1H), 7.81 (d, J=8.1 Hz, 1H), 7.77 (s, 1H), 7.69–7.62 (m, 4H), 7.34 (dd, J=8.3, 1.7 Hz, 2H), 3.18 (t, j=6.5 Hz, 2H), 2.89 (dd, J=6.9, 2.6 Hz, 1H), 1.18 (s, 3H), 1.20 (d, J=4.1 Hz, 3H), 2.53 (s, 3H), 2.51–2.38 (m, 2H).
APCI-MS m/z: 405.3[MH$^+$]

Example 50

2-(2,5-Dioxoimidazolidin-4-yl)-N-methyl-N-(2-phenylethyl)-acetamide

APCI-MS m/z: 276.2 [MH$^+$]

Example 51

N-[1-(4-Chlorophenyl)ethyl]-2-(2,5-dioxoimidazolidin-4-yl)-acetamide

APCI-MS m/z: 296.1 [MH$^+$]

Example 52

2-(2,5-Dioxoimidazolidin-4-yl)-N-(2-hydroxy-1-methyl-2-phenylethyl)-acetamide

APCI-MS m/z: 292.3[MH$^+$]

Example 53

N-{2-[4-(1,3-Benzodioxol-5-yl)phenyl]propyl}-2-(2,5-dioxoimidazolidin-4-yl)-acetamide APCI-MS m/z: 396.5 [MH$^+$]

Example 54

2-(2,5-Dioxoimidazoldin-4-yl)-N-[2-(3'-methoxybiphenyl-4-yl)propyl]-acetamide

APCI-MS m/z: 382.4 [MH$^+$]

Example 55

N-{2-[3'-(Acetylamino)biphenyl-4-yl]propyl}-2-(2,5-dioxoimidazolidin-4-yl)-acetamide APCI-MS m/z: 409.5 [MH$^+$]

Example 56

N-[2-(3'-Acetylbiphenyl-4-yl)propyl]-2-(2,5-dioxoimidazolidin-4-yl)-acetamide

APCI-MS m/z: 394.4 [MH$^+$]

Example 57

N-[2-(4'-Acetylbiphenyl-4-yl)propyl]-2-(2,5-dioxoimidazolidin-4-yl)-acetamide

APCI-MS m/z: 394.5 [MH$^+$]

Example 58

N-{2-[4-(1-Benzothien-2-yl)phenyl]propyl}-2-(2,5-dioxoimidazolidin-4-yl)-acetamide APCI-MS m/z: 408.4 [MH$^+$]

Example 59

N-[2-(3'-Cyanobiphenyl-4-yl)propyl]-2-(2,5-dioxoimidazolidin-4-yl)-acetamide

APCI-MS m/z: 377.4 [MH$^+$]

Example 60

N-[2-(4'-Cyanobiphenyl-4-yl)propyl]-2-(2,5-dioxoimidazolidin-4-yl)-acetamide

APCI-MS m/z: 377.4 [MH$^+$]

Example 61

2-(2,5-Dioxoimidazolidin-4-yl)-N-[2-(4'-fluoro-3'-methylbiphenyl-4-yl)propyl]-acetamide APCI-MS m/z: 384.4 [MH$^+$]

Example 62

2-(2,5-Dioxoimidazolidin-4-yl)-N-{2-[3'-(methylthio)biphenyl-4-yl]propyl}-acetamide APCI-MS m/z: 398.4 [MH$^+$]

Example 63

2-(2,5-Dioxoimidazolidin-4-yl)-N-{2-[4-(6-methoxypyridin-3-yl)phenyl]propyl}-acetamide APCI-MS m/z: 383.4 [MH$^+$]

Example 64

2-(2,5-Dioxoimidazolidin-4-yl)-N-[2-(4'-methoxy-3'-methylbiphenyl-4-yl)propyl]-acetamide APCI-MS m/z: 396.5 [MH$^+$]

Example 65

N-{2-[4-(2,3-Dihydro-1-benzofuran-5-yl)phenyl]propyl}-2-(2,5-dioxoimidazoldin-4-yl)-acetamide APCI-MS m/z: 394.5 [MH$^+$]

Example 66

2-(2,5-Dioxoimidazolidin-4-yl)-N-{2-[3'-(trifluoromethoxy)biphenyl-4-yl]propyl}-acetamide APCI-MS m/z: 436.5 [MH$^+$]

Example 67

N-[2-(3',4'-Dimethoxybiphenyl-4-yl)propyl]-2-(2,5-dioxoimidazoldin-4-yl)-acetamide APCI-MS m/z: 412.5 [MH$^+$]

Example 68

2-(2,5-Dioxoimidazolidin-4-yl)-N-[2-(4-quinolin-3-ylphenyl)propyl]-acetamide

APCI-MS m/z: 403.5 [MH$^+$]

Example 69

N-[2-(4'-Cyano-3'-methylbiphenyl-4-yl)propyl]-2-(2,5-dioxoimidazolidin-4-yl)-acetamide APCI-MS m/z: 391.5 [MH$^+$]

Example 70

N-[5-(1,3-Benzodioxol-5-yl)-2,3-dihydro-1H-inden-2-yl]-2-(2,5-dioxoimidazolidin-4-yl)-acetamide APCI-MS m/z: 394.4 [MH$^+$]

Example 71

2-(2,5-Dioxoimidazolidin-4-yl)-N-[5-(3-methoxyphenyl)-2,3-dihydro-1H-inden-2-yl]-acetamide APCI-MS m/z: 380.4 [MH$^+$]

Example 72

N-{5-[3-(Acetylamino)phenyl]-2,3-dihydro-1H-inden-2-yl}-2-(2,5-dioxoimidazoldin-4-yl)-acetamide APCI-MS m/z: 407.5 [MH$^+$]

Example 73

N-[5-(3-Acetylphenyl)-2,3-dihydro-1H-inden-2-yl]-2-(2,5-dioxoimidazolidin-4-yl)-acetamide APCI-MS m/z: 392.4 [MH$^+$]

Example 74

N-[5-(4-Acetylphenyl)-2,3-dihydro-1H-inden-2-yl]-2-(2,5-dioxoimidazolidin-4-yl)-acetamide APCI-MS m/z: 392.5 [MH$^+$]

Example 75

N-[5-(1-Benzothien-2-yl)-2,3-dihydro-1H-inden-2-yl]-2-(2,5-dioxoimidazolidin-4-yl)-acetamide APCI-MS m/z: 406.4 [MH$^+$]

Example 76

N-[5-(3-Cyanophenyl)-2,3-dihydro-1H-inden-2-yl]-2-(2,5-dioxoimidazolidin-4-yl)-acetamide APCI-MS m/z: 375.4 [MH$^+$]

Example 77

N-[5-(4-Cyanophenyl)-2,3-dihydro-1H-inden-2-yl]-2-(2,5-dioxoimidazolidin-4-yl)-acetamide APCI-MS m/z: 375.4 [MH$^+$]

Example 78

2-(2,5-Dioxoimidazolidin-4-yl)-N-[5-(4-fluoro-3-methylphenyl)-2,3-dihydro-1H-inden-2-yl]-acetamide APCI-MS m/z: 382.4 [MH$^+$]

Example 79

2-(2,5-Dioxoimidazolidin-4-yl)-N-{5-[3-(methylthio)phenyl]-2,3-dihydro-1H-inden-2-yl}-acetamide APCI-MS m/z: 396.4 [MH$^+$]

Example 80

2-(2,5-Dioxoimidazolidin-4-yl)-N-[5-(6-methoxypyridin-3-yl)-2,3-dihydro-1H-inden-2-yl]-acetamide APCI-MS m/z: 381.4 [MH$^+$]

Example 81

2-(2,5-Dioxoimidazolidin-4-yl)-N-[5-(4-methoxy-3-methylphenyl)-2,3-dihydro-1H-inden-2-yl)acetamide APCI-MS m/z: 394.5 [MH$^+$]

Example 82

N-[5-(2,3-Dihydro-1-benzofuran-5-yl)-2,3-dihydro-1H-inden-2-yl]-2-(2,5-dioxoimidazolidin-4-yl)acetamide APCI-MS m/z: 392.4 [MH$^+$]

Example 83

N-[5-(3,4-Dimethoxyphenyl)-2,3-dihydro-1H-inden-2-yl]-2-(2,5-dioxoimidazolidin-4-yl)-acetamide APCI-MS m/z: 410.5 [MH$^+$]

Example 84

N-[2-(4'-Fluorobiphenyl-4-yl)propyl]-2-(4-methyl-2,5-dioxoimidazolidin-4-yl)-acetamide APCI-MS m/z: 384.5 [MH$^+$]

Example 85

N-{2-[4-(1,3-Benzodioxol-5-yl)phenyl]propyl}-2-(4-methyl-2,5-dioxoimidazolidin-4-yl)-acetamide APCI-MS m/z: 410.5 [MH$^+$]

Example 86

N-[2-(3'-Methoxybiphenyl-4-yl)propyl]-2-(4methyl-2,5-dioxoimidazolidin-4-yl)-acetamide APCI-MS m/z: 396.5 [MH$^+$]

Example 87

N-{2-[4-(1-Benzothien-2-yl)phenyl]propyl}-2-(4-methyl-2,5dioxoimdazolidin-4-yl)-acetamide APCI-MS m/z: 422.5 [MH$^+$]

Example 88

N-[2-(3'-Cyanobiphenyl-4-yl)propyl]-2-(4-methyl-2,5-dioxoimidazolidin-4-yl)-acetamide APCI-MS m/z: 391.5 [MH$^+$]

Example 89

N-[2-(4'-Fluoro-3'-methylbiphenyl-4-yl)propyl]-2-(4-methyl-2,5-dioxoimidazolidin-4-yl)-acetamide APCI-MS m/z: 398.5 [MH$^+$]

Example 90

2-(4-Methyl-2,5-dioxoimidazolidin-4-yl)-N-{2-[3'-(methylthio)biphenyl-4-yl]propyl}-acetamide APCI-MS m/z: 412.5 [MH$^+$]

Example 91

N-{2-[4-(6-Methoxypyridin-3-yl)phenyl]propyl}-2-(4-methyl-2,5-dioxoimidazolidin-4-yl)-acetamide APCI-MS m/z: 397.5 [MH$^+$]

Example 92

N-[2-(4'-Methoxy-3'-methylbiphenyl-4-yl)propyl]-2-(4-methyl-2,5-dioxoimidazolidin-4-yl)-acetamide APCI-MS m/z: 410.5 [MH$^+$]

Example 93

N-{2-[4-(2,3-Dihydro-1-benzofuran-5-yl)phenyl]propyl}-2-(4-methyl-2,5-dioxoimidazolidin-4-yl)-acetamide APCI-MS m/z: 408.5 [MH$^+$]

Example 94

2-(4-Methyl-2,5-dioxoimidazolidin-4-yl)-N-{2-[3'-(trifluoromethoxy)biphenyl-4-yl]propyl}-acetamide APCI-MS m/z: 450.5 [MH$^+$]

Example 95

N-[2-(3',4'-Dimethoxybiphenyl-4-yl)propyl]-2-(4-methyl-2,5-dioxoimidazolidin-4-yl)-acetamide APCI-MS m/z: 426.5 [MH$^+$]

Example 96

2-(4-Methyl-2,5-dioxoimidazolidin-4-yl)-N-[2-(4-quinolin-3-ylphenyl)propyl]-acetamide APCI-MS m/z: 417.5 [MH$^+$]

Example 97

N-[5-(4-Fluorophenyl)-2,3-dihydro-1H-inden-2-yl]-2-(4-methyl-2,5-dioxoimidazolidin-4-yl)-acetamide APCI-MS m/z: 382.5 [MH$^+$]

Example 98

N-[5-(1,3-Benzodioxol-5-yl)-2,3-dihydro-1H-inden-2-yl]-2-(4-methyl-2,5-dioxoimidazolidin-4-yl)-acetamide APCI-MS m/z: 408.5 [MH$^+$]

Example 99

N-[5-(3-Methoxyphenyl)-2,3-dihydro-1H-inden-2-yl]-2-(4-methyl-2,5-dioxoimidazolidin-4-yl)-acetamide APCI-MS m/z: 394.5 [MH$^+$]

Example 100

N-{5-[3-(Acetylamino)phenyl]-2,3-dihydro-1H-inden-2-yl}-2-(4-methyl-2,5-dioxoimidazolidin-4-yl)-acetamide APCI-MS m/z: 421.5 [MH$^+$]

Example 101

N-[5-(3-Acetylphenyl)-2,3-dihydro-1H-inden-2-yl]-2-(4-methyl-2,5-dioxoimidazolidin-4-yl)-acetamide APCI-MS m/z: 406.5 [MH$^+$]

Example 102

N-[5-(4-Acetylphenyl)-2,3-dihydro-1H-inden-2-yl]-2-(4-methyl-2,5-dioxoimidazolidin-4-yl)-acetamide APCI-MS m/z: 406.5 [MH$^+$]

Example 103

N-[5-(1-Benzothien-2-yl)-2,3-dihydro-1H-inden-2-yl]-2-(4-methyl-2,5-dioxoimidazolidin-4-yl)-acetamide APCI-MS m/z: 420.5 [MH$^+$]

Example 104

N-[5-(3-Cyanophenyl)-2,3-dihydro-1H-inden-2-yl]-2-(4-methyl-2,5-dioxoimidazolidin-4-yl)-acetamide APCI-MS m/z: 389.5 [MH$^+$]

Example 105

N-[5-(4-Cyanophenyl)-2,3-dihydro-1H-inden-2-yl]-2-(4-methyl-2,5-dioxoimidazolidin-4-yl)-acetamide APCI-MS m/z: 389.5 [MH$^+$]

Example 106

N-[5-(4-Fluoro-3-methylphenyl)-2,3-dihydro-1H-inden-2-yl]-2-(4-methyl-2,5-dioxoimidazolidin-4-yl)-acetamide APCI-MS m/z: 396.5 [MH$^+$]

Example 107

2-(4-Methyl-2,5-dioxoimidazolidin-4-yl)-N-{5-[3-(methylthio)phenyl]-2,3-dihydro-1H-inden-2-yl}-acetamide APCI-MS m/z: 410.5 MH$^+$]

Example 108

N-[5-(6-Methoxypyridin-3-yl)-2,3-dihydro-1H-inden-2-yl]-2-(4-methyl-2,5-dioxoimidazolidin-4-yl)-acetamide APCI-MS m/z: 395.5 [MH$^+$]

Example 109

N-[5-(4-Methoxy-3-methylphenyl)-2,3-dihydro-1H-inden-2-yl]-2-(4-methyl-2,5-dioxoimidazolidin-4-yl)-acetamide APCI-MS m/z: 408.5 [MH$^+$]

Example 110

N-[5-(2,3-Dihydro-1-benzofuran-5-yl)-2,3-dihydro-1H-inden-2-yl]-2-(4-methyl-2,5-dioxoimidazolidin-4-yl)-acetamide APCI-MS m/z: 406.5 [MH$^+$]

Example 111

2-(4-Methyl-2,5-dioxoimidazolidin-4-yl)-N-{5-[3-(trifluoromethoxy)phenyl]-2,3-dihydro-1H-inden-2-yl}-acetamide APCI-MS m/z: 448.5 [MH$^+$]

Example 112

N-[5-(3,4-Dimethoxyphenyl)-2,3-dihydro-1H-inden-2-yl]-2-(4-methyl-2,5-dioxoimidazolidin-4-yl)-acetamide APCI-MS m/z: 424.5 [MH$^+$]

Example 113

N-[5-(4-Cyano-3-methylphenyl)-2,3-dihydro-1H-inden-2-yl]-2-(4-methyl-2,5-dioxoimidazolidin-4-yl)-acetamide APCI-MS m/z: 403.5 [MH$^+$]

Example 114

2-(2,5-Dioxoimidazolidin-4-yl)-N-(2-{4-[4 (trifluoromethyl)phenoxy]phenyl}ethyl)-acetamide a) [2-(4-Hydroxy-phenyl)-ethyl]-carbamic acid tert-butyl ester 2-(4-Hydroxyphenyl)-ethylamine (36.5 mmol, 5 g) was dissolved in 100 mL THF (dry, mol sieves) and di-tert-butyl dicarbonate (1.2eq 43.8 mmol, 9.5 g) was added slowly. The reaction mixture was stirred at room temperature for 1 hour before it was diluted with 700 mL ethyl acetate and washed with 500 mL sat. NaHCO$_3$/aq. The organic phase was dried over Na$_2$SO$_4$, filtrated and evaporated to dryness.

b) {2-[4-(4-Trifluoromethyl-phenoxy)-phenyl]-ethyl}carbamic acid tert-butyl ester 0.5 mmol of the BOC-protected amine obtained in a) above was dissolved in dichloromethane (5 mL) together with copper(II)acetate (0.5 mmol, 90 mg), powdered 4 Å mol sieves (app. 100 mg) and 4-(trifluoromethyl)benzeneboronic acid (1 mmol). After stirring the reaction mixture overnight at room temperature the slurry was filtered and purified by flash chromatography.

c) 2-[4-(4-Trifluoromethyl-phenoxy)-phenyl]-ethylamine

The BOC-group was removed by stirring the compound obtained in b) above in hydrochloric acid/THF (0.5 mL conc. HCl/1.5 mL THF) for 2 hours at room temperature before it was made basic by adding 10.5 mL 1M NaOH/aq. The free amine was extracted with 3×10 mL dichloromethane that was dried over Na$_2$SO$_4$, filtrated and evaporated to dryness. Yield 0.32 mmol (62%).

d) 2-(2,5-Dioxoimidazolidin-4-yl)-N-(2-{4-[4-(trifluoromethyl)phenoxy]-phenyl}ethyl)-acetamide The title compound was prepared by a method analogous to that described in Example 42e).

$^1$H NMR (400 MHz,DMSO-d$_6$): δ 10.55 (s, 1H), 8.05 (t, J=5.6 Hz, 1H), 7.79 (s, 1H), 7,72 (d, J=8.8 Hz, 2H), 7.30 (d, J=8.5 Hz, 2H), 7.08 (dd, J=20.1, 8.5 Hz, 4H), 4.20 (dd, J=6.2, 4.8 Hz, 1H), 3.29 (q, J=6.8 Hz, 2H), 2.73 (t, J=7.3 Hz, 2H), 2.57–2.36 (m, 2H).

APCI-MS m/z: 422.3 [MH$^+$]

The following compounds were prepared according to methods analogous to Example 114 above.

Example 115

2-(2,5-Dioxoimidazolidin-4-yl)-N-{2-[4-(4-methoxyphenoxy)phenyl]ethyl}-acetamide $^1$H NMR (400 MHz,DMSO-d$_6$): δ 10.54 (s, 1H), 8.01 (t, J=5.5 Hz, 1H), 7.77 (s, 1H), 7.16 (d, J=8.6 Hz, 2H), 6.97–6.91 (m, 4H), 6.83 (d, J=8.5 Hz, 2H), 4.18 (dd, J=6.2, 4.6 Hz, 1H), 3.72 (s, 3H), 3.22 (q, J=6.8 Hz, 2H), 2.65 (t, J=7.4 Hz, 2H), 2.55–2.33 (m, 2H).

APCI-MS m/z: 384.3 [MH$^+$]

Example 116

2-(2,5-Dioxoimidazolidin-4-yl)-N-(2-{4-[4-(trifluoromethoxy)phenoxy]phenyl}ethyl)-acetamide $^1$H NMR (400 MHz,DMSO-d$_6$): δ 10.55 (s, 1H), 8.04 (t, J=5.5 Hz, 1H), 7.79 (s, 1H), 7.37 (d, J=8.6 Hz, 2H), 7.25 (d, J=8.5 Hz, 2H), 7.07 (td, J=6.4, 4.0 Hz, 2H), 6.99 (d, j=8.5 Hz, 2H), 4.20 (dd, J=6.1, 4.7 Hz, 1H), 3.27 (q, J=6.8 Hz, 2H), 2.71 (t, J=7.4 Hz, 2H), 2.57–2.35 (m, 2H).

APCI-MS m/z: 438.3 [MH$^+$]

Example 117

N-{2-[4-(4-Chlorophenoxy)phenyl]ethyl}-2-(2,5-dioxoimidazolidin-4-yl)-acetamide $^1$H NMR (400 MHz,DMSO-d$_6$): δ 10.55 (s, 1H), 8.04 (t, J=5.5 Hz, 1H), 7.79 (s, 1H), 7.41 (dd, J=12.4, 3.5 Hz, 2H), 7.24 (d, J=8.5 Hz, 2H), 7.01–6.95 (m, 4H), 4.20 (dd, J=6.1, 4.7 Hz, 1H), 3.26 (q, J=6.8 Hz, 2H), 2.70 (t, J=7.4 Hz, 2H), 2.57–2.34 (m, 2H).

APCI-MS m/z: 388.3 [MH$^+$]

Example 118

N-{2-[4-(4-Acetylphenoxy)phenyl]ethyl}-2-(2,5-dioxoimidazolidin-4-yl)-acetamide $^1$H NMR (400 MHz,DMSO-d$_6$,): δ 10.55 (s, 1H), 8.05 (t, J=5.7 Hz, 1H), 7.97 (d, J=8.9 Hz, 2H), 7.80 (s, 1H), 7.29 (d, J=8.5 Hz, 2H), 7.04 (t, J=8.8 Hz, 4H), 4.22–4.19 (m, 1H), 3.33–3.24 (m, 2H), 2.73 (t, J=7.2 Hz, 2H), 2.58–2.35 (m, 5H).

APCI-MS m/z: 396.3 [MH$^+$]

Example 119

2-(2,5-Dioxoimidazolidin-4-yl)-N-{2-[4-(pyridin-3-yloxy)phenyl]ethyl}-acetamide

APCI-MS m/z: 355.3 [MH$^+$]

Example 120

2-(2,5-Dioxoimidazolidin-4-yl)-N-(2-{4-[(6-methoxypyridin-3-yl)oxy]phenyl}ethyl) -acetamide APCI-MS m/z: 385.1 [MH$^+$]

Example 121

N-{2-[4-(4-Cyanophenoxy)phenyl]ethyl}-2-(2,5-dioxoimidazolidin-4-yl)-acetamide $^1$H NMR (400 MHz,DMSO-d$_6$): δ 10.57 (s, 1H), 8.05 (t, J=5.5 Hz, 1H), 7.81 (d, J=8.9 Hz, 2H), 7.79 (s, 1H), 7.30 (d, J=8.5 Hz, 2H ), 7.06 (d, J=8.8 Hz, 4H), 4.20 (dd, J=6.1, 4.8 Hz, 1H ), 3.28 (q, J=6.7 Hz, 2H), 2.73 (t, J=7.3 Hz, 2H), 2.56–2.36 (m, 2H).

APCI-MS m/z: 379.3 [MH$^+$]

Example 122

2-(2,5-Dioxoimidazolidin-4-yl)-N-{2-[4-(4-methylphenoxy)phenyl]ethyl}-acetamide $^1$H NMR (400 MHz, DMSO-d$_6$): δ 10.55 (s, 1H), 8.03 (t, J=5.5 Hz, 1H), 7.79 (s, 1H), 7.21–7.16 (m, 4H), 6.89 (d, J=8.2 Hz, 4H), 4.20 (dd, J=6.0, 4.5Hz, 1H), 3.25 (q, J=6.8 Hz, 2H), 2.68 (t, J=7.4 Hz, 2H), 2.56–2.35 (m, 2H), 2.28 (s, 3H).

APCI-MS m/z: 368.3 [MH$^+$]

Example 123

2-(2,5-Dioxoimidazolidin-4-yl)-N-{2-[4-(4-fluorophenoxy)phenyl]ethyl}-acetamide $^1$H NMR (400 MHz,DMSO-d$_6$): δ 10.53 (s, 1H), 8.02 (t, J=5.5 Hz, 1H), 7.77 (s, 1H), 7.23–7.17 (m, 4H), 7.02 (tt, J=4.5, 2.3 Hz, 2H), 6.90 (d, J=8.5 Hz, 2H), 4.18 (dd, J=6.0, 4.7 Hz, 1H), 3.24 (q, J=6.8 Hz, 2H), 2.67 (t, J=7.3 Hz, 2H), 2.54–2.33 (m, 2H).

APCI-MS m/z: 372.3 [MH$^+$]

Example 124

N-(2-Biphenyl-4-yl-2hydroxy-ethyl)-2-(2,5-dioxoimidazolidin-4-yl)-acetamide a) 4-Phenylphenyloxirane 4-Phenyl-(α-bromoacetophenone), 8.25 g (0.030 mol), was slurried in methanol (150 mL). Sodium borohydride (3.80 g; 0.10 mol) was added in portions to give an exothermal is reaction and a homogeneous reaction mixture. After 20 hours, water (600 mL) was added and the mixture was extracted with dichloromethane (500 mL). The organic phase was evaporated to give 7.25 g of crude product. NMR analysis showed mainly a 1:1 mixture of epoxide and vicinal bromo alcohol.

b) 2-Amino-1-biphenyl-4-yl-ethanol

The product mixture obtained in a) above was dissolved in THF (ca 100 mL) and a large excess of concentrated ammonia and ethanol was added to give a homogeneous system. TLC analysis after 4 hours showed only starting materials. A slight increase in temperature gave scarce improvement and the mixture was finally heated to 70° C. in a sealed vessel for 20 hours. TLC analysis showed absence of starting materials and NMR analysis showed a complex mixture of products. The solvents were evaporated and dichloromethane (150 mL) was added to give a precipitate. The mixture was filtered and the solid, about 3.8 g, and filtrate was analysed with TLC and NMR. Analyses showed mixtures of products but with, possibly, expected product in the solid phase. A sample of the solid (1.04 g) was purified by silica gel chromatography (200 mL) using dichloromethane/methanol/concentrated ammonia (90+10+1) as eluant. Evaporation of pure fractions gave 0.62 g of the sub-titled compound.

N-(2-Biphenyl-4-yl-2-hydroxy-ethyl)-2-(2,5-dioxoimidazolidin-4-yl)-acetamide

The title compound was prepared by a method analogous to that described in Example 42e).

$^1$H NMR (400 MHz,DMSO-d$_6$): δ 10.57 (s, 1H), 8.10 (q, J=5.8 Hz, 1H), 7.79 (s, 1H), 7.64 (t, J=8.5 Hz, 4H), 7.45 (q, J=7.7 Hz, 4H), 7.35 (t, J=7.3 Hz, 1H), 5.49 (s, 1H), 4.66 (t, J=3.7 Hz, 1H), 4.26–4.17 (m, 1H), 3.20–3.09 (m, 1H), 2.59 (dt, J=15.5, 3.5 Hz, 1H), 2.52–2.39 (m, 2H).

APCI-MS m/z: 336.3 [MH$^+$]

Example 125

N-[2-(1,1'-Biphenyl-4-yl)-2-methoxyethyl]-2-(2,5-dioxoimidazolidin-4-yl)-acetamide a) 4-(2-Amino-1-methoxyethyl)-biphenyl 4-Vinyl-biphenyl, 1.70 g (9.4 mmol), was dissolved in methanol (10 mL) and dichloromethane (15 mL). Bromine, 0.48 mL (9.4 mmol), dissolved in methanol (10 mL) was added over 30 minutes and TLC analysis showed complete reaction. The mixture was diluted with dichloromethane and added to an aqueous solution of sodium hydrogen sulphite and the mixture was shaken. The dichloromethane phase was washed with aqueous sodium hydrogen carbonate and water and evaporated to give 2.81 g product. The product was purified by silica gel chromatography silica gel (200 mL) with heptane/ethyl acetate (95+5) to give 1.00 g (39%) of pure 4-(2-bromo-1-methoxy-ethyl)-biphenyl. 4-(2-Bromo-1-methoxyethyl)-biphenyl, 1.00 g (3.64 mmol), was dissolved in ethanol (20 mL) and added to a large excess of concentrated ammonia (20 mL). The mixture was heated to 100° C. in a sealed vessel for 16 hours and evaporated. Chromatography on silica gel (180 mL) with dichloromethane followed by dichloromethane/methanol/concentrated ammonia (90+10+1) gave 0.47 g (61%) of the sub-titled compound.

b) N-[2-(1,1'-Biphenyl-4-yl)-2-methoxyethyl]-2-(2,5-dioxoimidazolidin-4-yl)-acetamide The title compound was prepared by a method analogous to that described in Example 42e).

$^1$H NMR (400 MHz, DMSO-$d_6$): δ 10.56 (s, 1H), 8.16 (d, J=5.5 Hz, 1H), 7.78 (d, J=6.2 Hz, 1H), 7.70–7.64 (m, 4H), 7.47 (t, J=7.6 Hz, 2H), 7.42–7.34 (m, 3H), 4.29 (dt, J=7.8, 5.0 Hz, 1H), 4.23–4.19 (m, 1H), 3.19 (s, 3H), 2.61–2.53 (m, 2H), 2.50–2.39 (m, 2H).

APCI-MS m/z: 368.2 [MH$^+$]

Example 126

N-[2-(1,1'-Biphenyl-4-yl)-ethyl]-2-(2,5-dioxoimidazolidin-4-yl)-N-methylacetamide a) (4-Phenylphenethyl)-N-methylamine 4-Phenylphenethyl amine, 0.48 g (2.4 mmol), was added to an excess of methyl formate (5 mL) and dichloromethane (5 mL) was added to improve solubility. The heterogeneous reaction mixture was refluxed to give a solution within 20 hours. NMR analysis of a sample showed almost complete conversion to N-formyl amine. The reaction mixture was evaporated to give 0.47 g (87%). The formyl compound, 0.47 g (2.09 mmol), was dissolved in THF and 2.1 mL of 1.0 M lithium aluminium hydride (2.1 mmol) in THF was added. TLC analysis after 20 hours showed only starting material and 2 mL (2 mmol) of lithium aluminium hydride solution was added. Analysis after 1 hour showed starting material and the mixture was heated to reflux. After 1.5 hours a precipitate was formed, the starting material consumed and tetrahydrofuran (15 ml) was added. The mixture was quenched by successive addition of water (0.15 g), 15% aqueous sodium hydroxide (0.15 g) and water (0.45 g). The mixture was filtered and evaporated to give 0.33 g crude product. The crude product was purified by silica gel chromatography (100 mL) using dichloromethane/methanol/concentrated ammonia (90+10+1) as eluant. Evaporation of pure fractions gave 78 mg (18%) of the sub-titled compound.

b) N-[2-(1,1'-Biphenyl-4-yl)-ethyl]-2-(2,5-dioxoimidazolidin-4-yl)-N-methylacetamide The title compound was prepared by a method analogous to that described in Example 42e).

APCI-MS m/z: 352.3 [MH$^+$]

Example 127

2-(2,5-Dioxoimidazolidin-4-yl)-N-[2-(4-phenylethynyl-piperidin-1-yl)ethyl]-acetamide a) 4-(Phenylethynyl)piperidine N-BOC4-ethynylpiperidin, 0.5 g (2.40 mmol), and iodobenzene, 0.29 mL (2.64 mmol) were dissolved in triethylamine (9 mL) and argon was passed through for a few minutes. Copper(I) iodide, 0.087 g (0.5 mmol), and bis[triphenylphosphine]palladium dichloride, 0.070 g (0.1 mmol), were added and the mixture was heated to 82° C. in a closed vessel for 17 hours. TLC analysis indicated complete reaction. Triethylamine was evaporated and the mixture was purified by silica gel chromatography (75 mL) using heptane/ethyl acetate (4+1) as eluant. Evaporation of pure fractions gave 0.497 g (73%) of N-BOC4-(phenylethynyl)piperidine. The protected piperidine, 0.497 g (1.74 mmol), was dissolved in dichloromethane and trifluoroacetic acid (1 mL) was added. The reaction was completed within 20 hours and the mixture was evaporated to give an oil. NMR analysis showed pure ammonium trifluoroacetate, contaminated with trifluoroacetic acid. The product was dissolved in dichloromethane and extracted with aqueous sodium hydrogen carbonate and water. Evaporation of solvent gave 0.284 g (88%) of the sub-titled compound.

b) 2-[4-(Phenylethynyl)piperidin-1-yl]ethanamine 4-(Phenylethynyl)piperidine (0.5 mmol, 92 mg) was dissolved in acetonitrile (anhydrous 4 Å, 4 mL) together with bromoethylphtalimide (0.5 mmol, 128 mg) and $K_2CO_3$ (2 mmol, 276 mg). The reaction mixture was heated to reflux for 3 hours, diluted with ethyl acetate (50 mL) and washed with HCl/aq (1M, 50 mL). The organic phase was dried over $Na_2SO_4$, filtered and evaporated to dryness. The protection group was removed by stirring the compound in methylamine (33% in ethanol, 5 mL) for another 3 hours. The mixture was evaporated, diluted with ethyl acetate (50 mL) and washed with NaOH (1M, 50 mL). The organic phase was dried over $Na_2SO_4$, filtered and evaporated to dryness. The crude product was used without further purification.

c) 2-(2,5-Dioxoimidazolidin-4-yl)-N-[2-(4-phenylethynyl-piperidin-1-yl)ethyl]-acetamide The title compound was prepared by a method analogous to that described in Example 42e).

$^1$H NMR (400 MHz, CDCl$_3$): δ 9.96 (s, 1H), 9.67 (s, 1H), 8.23 (s, 1H), 7.34 (dd, J=66.3, 28.1 Hz, 5H), 4.35 (s, 1H), 3.82–1.88 (m, 15H).

APCI-MS m/z: 369.3 [MH$^+$]

Example 128

N-{2-[(4-Bromobenzyl)oxy]ethyl}-2-(2,5-dioxoimidazolidin-4-yl)-acetamide a) 2-(4-Bromo-benzyloxy)-ethylamine hydrochloride Sodium hydride (60% in oil, 0.613 g, 15 mmol) was added in small portions over 5 minutes to a solution of tert-butyl N-(2-hydroxyethyl)-carbamate (1.771 g, 10.99 mmol), 4-bromobenzylbromide (2.676 g, 10.708 mmol) in dimethyl formaide (50 ml). The mixture was stirred for 2 hours at ambient temperature under argon. The mixture was partitioned between water (250 mL), ethyl acetate (50 mL) and heptane (50 mL). The organic phase was washed two times with water (30 mL). Evaporation afforded 3.13 g of a clear oil. The oil was stirred in 2.5 M HCl in ethyl acetate (50 mL) for 2 hours. Filtering and washing with ethyl acetate afforded the sub-titled compound (2.256 g, 98.1% yield).

$^1$HNMR (300 MHz, DMSO-$d_6$): δ 8.16 (3H, bs); 7.55 (2H, d); 7.36 (2H, d); 4.51 (2H, s); 3.64 (2H, t); 2.99 (2H, t).

APCI-MS m/z: 229.9; 231.9 [MH$^+$]

b) N-{2-[(4-bromobenzyl)oxy]ethyl}-2-(2,5-dioxoimidazolidin-4-yl)-acetamide

The title compound was prepared by a method analogous to that described in Example 42e).

$^1$HNMR (300 MHz, DMSO-$d_6$): δ 10.56 (1H, s); 8.08 (1H, t); 7.81 (1H, s); 7.54 (1H, d); 7.30 (1H, d); 4.45 (2H, s); 4.20 (1H, m); 3.25 (2H, q); 2.50 (2H, p); 2.50 (2H, m).

APCI-MS m/z: 370; 372 [MH$^+$]

Example 129

2-(1,1'-Biphenyl-4-yl)-2-oxoethyl (2,5-dioxoimidazolidin-4-yl)acetate

Hydantoin acetic acid (109 mg, 0.69 mmol), 2-bromo-4'-phenylacetophenone (191 mg, 0.69 mmol) and N-ethyldiisopropylamine (120 μl, 0.70 mmol) were stirred in dimethylformamide (5.0 mL) at 50° C. for 3 hours. Evaporation and chromatography on silica (dichloromethane/methanol: 100/3) afforded 123 mg of the title compound in 50.1% yield.

$^1$HNMR (300 MHz, DMSO-$d_6$,): δ 10.68 (H, s); 8.06 (2H, d); 7.90 (1H, s); 7.87 (2H, d); 7.77 (2H, d); 7.55–7.42 (3H, m); 5.55 (2H, d); 4.32 (1H, dt); 2.90 (2H, d).

APCI-MS m/z: 353.1 [MH$^+$]

Pharmacological Example

Isolated Enzyme Assay

Recombinant human MMP12 catalytic domain may be expressed and purified as described by Parkar A. A. et al, (2000), Protein Expression and Purification, 20:152. The purified enzyme can be used to monitor inhibitors of activity as follows: MMP12 (50 ng/ml final concentration) is incubated for 60 minutes at room temperature with the synthetic substrate Mac-Pro-Cha-Gly-Nva-His-Ala-Dpa-NH$_2$ in assay buffer (0.1M "Tris-HCl" (trade mark) buffer, pH 7.3 containing 0.1M NaCl, 20 mM CaCl$_2$, 0.020 mM ZnCl and 0.05% (w/v) "Brij 35 " (trade mark) detergent) in the presence (5 concentrations) or absence of inhibitors. Activity is determined by measuring the fluorescence at λex 320 nm and λem 405 nm. Percent inhibition is calculated as follows: % Inhibition is equal to the [Fluorescence$_{plus\ inhibitor}$–Fluorescence$_{background}$] divided by the [Fluorescence$_{minus\ inhibitor}$–Fluorescene$_{background}$].

For example, the following table shows the IC$_{50}$ figures for a representative selection of compounds according to the invention when tested in the MMP12 enzyme assay.

| Compound of Example No. | Human MMP12 IC$_{50}$ (μm) |
|---|---|
| 1 | 0.022 |
| 2 | 0.007 |
| 5 | 0.032 |

-continued

| Compound of Example No. | Human MMP12 IC$_{50}$ (μm) |
|---|---|
| 14 | 0.006 |
| 21 | 0.008 |
| 22 | 0.015 |
| 23 | 0.006 |
| 24 | 0.004 |
| 26 | 0.017 |
| 27 | 0.005 |

The invention claimed is:

1. A compound of formula (I) or a pharmaceutically acceptable salt or solvate thereof

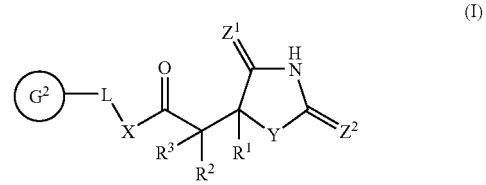

(I)

wherein

X represents a group NR$^4$;

Y represents NH or N-methyl;

Z$^1$ and Z$^2$ each independently represent an oxygen or sulphur atom, provided that at least one of Z$^1$ and Z$^2$ represents an oxygen atom;

Either R$^1$ represents hydrogen or a group selected from C$_1$–C$_6$ alkyl and a saturated or unsaturated 3- to 10-membered ring system which may comprise at least one ring heteroatom selected from nitrogen, oxygen and sulphur, each group being optionally substituted with at least one substituent selected from halogen, hydroxyl, cyano, carboxyl, —NR$^5$R$^6$, —CONR$^7$R$^8$, C$_1$–C$_6$ alkyl, C$_1$–C$_6$ alkoxy, C$_1$–C$_6$ alkylcarbonyl(oxy), —S(O)$_m$C$_1$–C$_6$ alkyl where m is 0, 1 or 2, C$_1$–C$_6$ alkylsulphonylamino, C$_1$–C$_6$ alkoxycarbonyl(amino), benzyloxy and a saturated or unsaturated 5- to 6-membered ring which may comprise at least one ring heteroatom selected from nitrogen, oxygen and sulphur, the ring in turn being optionally substituted with at least one substituent selected from halogen, hydroxyl, oxo, carboxyl, cyano, C$_1$–C$_6$ alkyl, C$_1$–C$_6$ alkoxycarbonyl and C$_1$–C$_6$ hydroxyalkyl, R$^2$ represents hydrogen or C$_1$–C$_6$ alky, and R$^3$ represents hydrogen or C$_1$–C$_6$ alkyl, or R$^1$ and R$^2$ together with the carbon atoms to which they are attached form a saturated 5- to 6-membered ring optionally comprising a ring heteroatom selected from nitrogen, oxygen and sulphur, and R$^3$ is as defined above, or R$^2$ and R$^3$ together with the carbon atom to which they are attached form a saturated 5- to 6-membered ring optionally comprising a ring heteroatom selected from nitrogen, oxygen and sulphur, and R$^1$ is as defined above;

R$^4$ represents hydrogen or C$_1$–C$_6$ alkyl;

R$^5$, R$^6$,R$^7$ and R$^8$ each independently represent hydrogen or C$_1$–C$_6$ alkyl optionally substituted by at least one substituent selected from hydroxyl, halogen and C$_1$–C$_6$ alkoxy;

L represents a $C_2$–$C_6$ alkyl optionally interrupted or terminated by at least one moiety selected from O, NH, S, SO, $SO_2$ and C(O) the $C_2$–$C_6$ alkyl group being optionally substituted with at least one substituent selected from hydroxyl, halogen, $C_1$–$C_4$ alkyl, $C_1$–$C_4$ haloalkyl, $C_1$–$C_4$ alkoxy and $C_1$–$C_4$ haloalkoxy;

$G^2$ represents a saturated or unsaturated 5- to 10-membered ring system which may comprise at least one ring heteroatom selected from nitrogen, oxygen and sulphur, the ring system being optionally substituted with at least one substituent selected from halogen, hydroxyl, cyano, nitro, $C_1$–$C_6$ alkyl (optionally substituted by one or more of cyano, halogen, hydroxyl and methoxy), $C_2$–$C_6$ alkenyl, $C_1$–$C_6$ alkoxy (optionally substituted by one or more halogen atoms), —S(O)$_n$ $C_1$–$C_6$ alkyl where n is 0, 1 or 2, $C_1$–$C_6$ alkylcarbonyl (amino), $C_1$–$C_6$ alkylcarbonyloxy, phenyl, benzyloxy, —$NR^9R^{10}$ and a group of formula

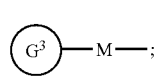

(II)

$R^9$ and $R^{10}$ each independently represent hydrogen or $C_1$–$C_6$ alkyl optionally substituted by at least one substituent selected from hydroxyl, halogen and $C_1$–$C_6$ alkoxy;

M represents a bond or —O—, —S—, —C≡C—, —$CH_2$O— or —$OCH_2$—;

$G^3$ represents an unsaturated 5- to 10-membered ring system which may comprise at least one ring heteroatom selected from nitrogen, oxygen and sulphur, the ring system being optionally substituted with at least one substituent selected from halogen, hydroxyl, cyano, nitro, $C_1$–$C_6$ alkyl (optionally substituted by one or more of cyano, halogen, hydroxyl and methoxy), $C_2$–$C_6$ alkenyl, $C_1$–$C_6$ alkoxy (optionally substituted by one or more halogen atoms), —S(O)$_t$$C_1$–$C_6$ alkyl where t is 0, 1 or 2, $C_1$–$C_6$ alkylcarbonyl(amino), $C_1$–$C_6$ alkylcarbonyloxy, phenyl, benzyloxy and —$NR^{11}R^{12}$; and $R^{11}$ and $R^{12}$ each independently represent hydrogen or $C_1$–$C_6$ alkyl optionally substituted by at least one substituent selected from hydroxyl, halogen and $C_1$–$C_6$ alkoxy.

2. A compound according to claim 1, wherein $R^4$ represents hydrogen.

3. A compound according to claim 1, wherein Y represents NH.

4. A compound according to claim 1, wherein $Z^1$ and $Z^2$ both represent an oxygen atom.

5. A compound according to claim 1, wherein L represents a $C_2$–$C_4$ alkyl group optionally interrupted or terminated by one or two moieties independently selected from O, NH, S, SO, $SO_2$ and C(O), $C_2$–$C_4$ alkyl group being optionally substituted with one or two substituents independently selected from hydroxyl, halogen, $C_1$–$C_4$ alkyl, $C_1$–$C_4$ haloalkyl, $C_1$–$C_4$ alkoxy and $C_1$–$C_4$ haloalkoxy.

6. A compound according to claim 1, wherein, in $G^2$, the saturated or unsaturated 5- to 10-membered ring system is selected from cyclopentyl, cyclohexyl, bicyclo[2.2.1]heptyl, cyclopentenyl, cyclohexenyl, phenyl, pyrrolidinyl, piperidinyl, piperazinyl, morpholinyl, thiomorpholinyl, diazabicyclo[2.2.1]hept-2-yl, naphthyl, benzofuranyl, benzothienyl, benzodioxolyl, quinolinyl, 2,3-dihydrobenzofuranyl, tetrahydropyranyl, pyrazolyl, pyrazinyl, thiazolidinyl, indanyl, thienyl, isoxazolyl, pyridazinyl, thiadiazolyl, pyrrolyl, furanyl, thiazolyl, indolyl, imidazolyl, pyrimidinyl, benzimidazolyl, triazolyl, tetrazolyl and pyridinyl.

7. A compound according to claim 1, wherein, in $G^3$, the unsaturated 5- to 10-membered ring system is selected from cyclopentenyl, cyclohexenyl, phenyl, naphthyl, benzofuranyl, benzothienyl, benzodioxolyl, quinolinyl, 2,3-dihydrobenzofuranyl, pyrazolyl, pyrazinyl, thiazolidinyl, indanyl, thienyl, isoxazolyl, pyridazinyl, thiadiazolyl, pyrrolyl, furanyl, thiazolyl, indolyl, imidazolyl, pyrimidinyl, benzimidazolyl, triazolyl, tetrazolyl and pyridinyl.

8. A compound according to claim 1 which is selected from the group consisting of:

2-(2,5-Dioxoimidazolidin-4-yl)-N-[2-(4'-fluoro-biphenyl-4-yl)-ethyl]-acetamide,

N-[2-(4'-Cyano-biphenyl-4-yl)-ethyl]-2-(2,5-dioxoimidazolidin-4-yl)-acetamide,

N-[2-(4-Chlorophenyl)ethyl]-2-(2,5-dioxoimidazolidin-4-yl)-acetamide,

N-(2-Biphenyl-4-yl-ethyl)-2-(2,5-dioxoimidazolidin-4-yl)-acetamide, 2-(2,5-Dioxoimidazolidin-4-yl)-N-[2-(7-methyl-1H-indol-3-yl)ethyl]-acetamide, 2-(2,5-Dioxoimidazolidin-4-yl)-N-[2-(4-phenoxyphenyl) ethyl]-acetamide, 2-(2,5-Dioxoimidazolidin-4-yl)-N-[2-(4-fluorophenyl) ethyl]-acetamide, N-[2-(4-Bromophenyl)ethyl]-2-(2,5-dioxoimidazolidin-4-yl)-acetamide, N-[2-(2,4-Dichlorophenyl)ethyl]-2-(2,5-dioxoimidazolidin-4-yl)-acetamide, N-[2-(3'-Chloro-biphenyl-4-yl)-ethyl]-2-(2,5-dioxoimidazolidin-4-yl)-acetamide, N-[2-(4'-Benzyloxy-biphenyl-4-yl)-ethyl]-2-(2,5-dioxoimidazolidin-4-yl)-acetamide, 2-(2,5-Dioxoimidazolidin-4-yl)-N-[2-(4-thiophen-3-yl-phenyl)ethyl]-acetamide, 2-(2,5-Dioxoimidazolidin-4-yl)-N-[2-(4-thiophen-2-yl-phenyl)ethyl]-acetamide, N-[2-(4'-Chloro-biphenyl-4-yl)-ethyl]-2-(2,5-dioxoimidazolidin-4-yl)-acetamide, 2-(2,5-Dioxoimidazolidin-4-yl)-N-[2-(4-methylsulfanyl-biphenyl-4-yl)ethyl]-acetamide, 2-(2,5-Dioxoimidazolidin-4-yl)-N-[2-(3'-nitro-biphenyl-4-yl)ethyl]-acetamide, 2-(2,5-Dioxoimidazolidin-4-yl)-N-[2-(4'-methyl-biphenyl-4-yl)ethyl]-acetamide, N-[2-(3'-Acetylamino-biphenyl-4-yl)ethyl]-2-(2,5-dioxoimidazolidin-4-yl)-acetamide, 2-(2,5-Dioxoimidazolidin-4-yl)-N-[2-(4-naphthalen-2-yl-phenyl)ethyl]-acetamide, N-[2-(3',5'-Dichloro-biphenyl-4-yl)ethyl]-2-(2,5-dioxoimidazolidin-4-yl)-acetamide, 2-(2,5-Dioxoimidazolidin-4-yl)-N-[2-(3'-methyl-biphenyl-4-yl)ethyl]-acetamide, N-[2-(4-Benzofuran-2-yl-phenyl)ethyl]-2-(2,5-dioxoimidazolidin-4-yl)-acetamide, 2-(2,5-Dioxoimidazolidin-4-yl)-N-[2-(3'-methoxy-biphenyl-4-yl)ethyl]-acetamide, 2-(2,5-Dioxoimidazolidin-4-yl)-N-(2-[1,1';4', 1"]terphenyl-4-ylethyl)-acetamide, N-[2-(4'-Acetyl-biphenyl-4-yl)ethyl]-2-(2,5-dioxoimidazolidin-4-yl)-acetamide, N-[2-(4-Benzo[b]thiophen-2-yl-phenyl)ethyl]-2-(2,5-dioxoimidazolidin-4-yl)-acetamide, N-[2-(4'-Cyanomethyl-biphenyl-4-yl)ethyl]-2-(2,5-dioxoimidazolidin-4-yl)-acetamide,
2-(2,5-Dioxoimidazolidin-4-yl)-N-[2-(4-pyridin-3-ylphenyl)ethyl]-acetamide,
2-(2,5-Dioxoimidazolidin-4-yl)-N-{2-[4-(1H-pyrrol-2-yl)phenyl]ethyl}-acetamide,
2-(2,5-Dioxoimidazolidin-4-yl)-N-[2-(4-furan-3-yl-phenyl)ethyl]-acetamide,
2-(2,5-Dioxoimidazolidin-4-yl)-N-[2-(4-furan-2-yl-phenyl)ethyl]-acetamide,
2-(2,5-Dioxoimidazolidin-4-yl)-N-(2-thiophen-2-yl-ethyl)-acetamide,
N-[2-(4-tert-Butylphenyl)ethyl]-2-(2,5-dioxoimidazolidin-4-yl)-acetamide,
N-[2-(4-Chlorophenyl)-1-methylethyl]-2-(2,5-dioxoimidazolidin-4-yl)acetamide,
N-[2-(4-Chlorophenyl)ethyl]-2-(4-methyl-2,5-dioxoimidazolidin-4-yl)acetamide,
N-[2-(4-Chlorophenyl)propyl]-2-(4-methyl-2,5-dioxoimidazolidin-4-yl)acetamide,
N-[2-(4'-Cyano-1,1'-biphenyl-4-yl)ethyl]-2-(4-methyl-2,5-dioxoimidazolidin-4-yl)acetamide,
N-[2-(4'-Fluoro-1,1'-biphenyl-4-yl)ethyl]-2-(4-methyl-2,5-dioxoimidazolidin-4-yl)acetamide,
2-(2,5-Dioxoimidazolidin-4-yl)-N-[2-(4'-fluoro-1,1'-biphenyl-4-yl)propyl]-acetamide,
N-[2-(4'-Cyanobiphenyl-4-yl)propyl]-2-(4-methyl-2,5-dioxoimidazolidin-4-yl)-acetamide,
2-(2,5-Dioxoimidazolidin-4-yl)-N-[2-(3'-methoxybiphenyl-4-yl)ethyl]-acetamide,
N-[2-(4'-Cyano-3'-methylbiphenyl-4-yl)propyl]-2-(4-methyl-2,5-dioxoimidazolidin-4-yl)-acetamide,
2-(2,5-Dioxoimidazolidin-4-yl)-N-methyl-N-(2-phenylethyl)-acetamide,
N-[1-(4-Chlorophenyl)ethyl]-2-(2,5-dioxoimidazolidin-4-yl)-acetamide,
2-(2,5-Dioxoimidazolidin-4-yl)-N-(2-hydroxy-1-methyl-2-phenylethyl)-acetamide,
N-{2-[4-(1,3-Benzodioxol-5-yl)phenyl]propyl}-2-(2,5-dioxoimidazolidin-4-yl)-acetamide,
2-(2,5-Dioxoimidazolidin-4-yl)-N-[2-(3'-methoxybiphenyl-4-yl)propyl]-acetamide,
N-{2-[3'-(Acetylamino)biphenyl-4-yl]propyl}-2-(2,5-dioxoimidazolidin-4-yl)-acetamide,
N-[2-(3'-Acetylbiphenyl-4-yl)propyl]-2-(2,5-dioxoimidazolidin-4-yl)-acetamide,
N-[2-(4'-Acetylbiphenyl-4-yl)propyl]-2-(2,5-dioxoimidazolidin-4-yl)-acetamide,
N-{2-[4-(1-Benzothien-2-yl)phenyl]propyl}-2-(2,5-dioxoimidazolidin-4-yl)-acetamide,
N-[2-(3'-Cyanobiphenyl-4-yl)propyl]-2-(2,5-dioxoimidazolidin-4-yl)-acetamide,
N-[2-(4'-Cyanobiphenyl-4-yl)propyl]-2-(2,5-dioxoimidazolidin-4-yl)-acetamide,
2-(2,5-Dioxoimidazolidin-4-yl)-N-[2-(4'-fluoro-3'-methylbiphenyl-4-yl)propyl]-acetamide,
2-(2,5-Dioxoimidazolidin-4-yl)-N-{2-[3'-(methylthio)biphenyl-4-yl]propyl}-acetamide,
2-(2,5-Dioxoimidazolidin-4-yl)-N-{2-[4-(6-methoxypyridin-3-yl)phenyl]propyl}-acetamide,
2-(2,5-Dioxoimidazolidin-4-yl)-N-[2-(4'-methoxy-3'-methylbiphenyl-4-yl)propyl]-acetamide,
N-{2-[4-(2,3-Dihydro-1-benzofuran-5-yl)phenyl]propyl}-2-(2,5-dioxoimidazolidin-4-yl)-acetamide,
2-(2,5-Dioxoimidazolidin-4-yl)-N-{2-[3'-(trifluoromethoxy)biphenyl-4-yl]propyl}-acetamide,
N-[2-(3',4'-Dimethoxybiphenyl-4-yl)propyl]-2-(2,5-dioxoimidazolidin-4-yl)-acetamide,
2-(2,5-Dioxoimidazolidin-4-yl)-N-[2-(4-quinolin-3-ylphenyl)propyl]-acetamide,
N-[2-(4'-Cyano-3'-methylbiphenyl-4-yl)propyl]-2-(2,5-dioxoimidazolidin-4-yl)-acetamide,
N-[2-(4'-Fluorobiphenyl-4-yl)propyl]-2-(4-methyl-2,5-dioxoimidazolidin-4-yl)-acetamide,
N-{2-[4-(1,3-Benzodioxol-5-yl)phenyl]propyl}-2-(4-methyl-2,5-dioxoimidazolidin-4-yl)-acetamide,
N-[2-(3'-Methoxybiphenyl-4-yl)propyl]-2-(4-methyl-2,5-dioxoimidazolidin-4-yl)-acetamide,
N-{2-[4-(1-Benzothien-2-yl)phenyl]propyl}-2-(4-methyl-2,5-dioxoimidazolidin-4-yl)-acetamide,
N-[2-(3'-Cyanobiphenyl-4-yl)propyl]-2-(4-methyl-2,5-dioxoimidazolidin-4-yl)-acetamide,
N-[2-(4'-Fluoro-3'methylbiphenyl-4-yl)propyl]-2-(4-methyl-2,5-dioxoimidazolidin-4-yl)-acetamide,
2-(4-Methyl-2,5-dioxoimidazolidin-4-yl)-N-{2-[3'-(methylthio)biphenyl-4-yl]propyl}-acetamide,
N-{2-[4-(6-Methoxypyridin-3-yl)phenyl]propyl}-2-(4-methyl-2,5-dioxoimidazolidin-4-yl)-acetamide,
N-[2-(4'-Methoxy-3'-methylbiphenyl-4-yl)propyl]-2-(4-methyl-2,5-dioxoimidazolidin-4-yl)-acetamide,
N-{2-[4-(2,3-Dihydro-1-benzofuran-5-yl)phenyl]propyl}-2-(4-methyl-2,5-dioxoimidazolidin-4-yl)-acetamide,
2-(4-Methyl-2,5-dioxoimidazolidin-4-yl)-N-{2-[3'-(trifluoromethoxy)biphenyl-4-yl]propyl}-acetamide,
N-[2-(3',4'-Dimethoxybiphenyl-4-yl)propyl]-2-(4-methyl-2,5-dioxoimidazolidin-4-yl)-acetamide,
2-(4-Methyl-2,5-dioxoimidazolidin-4-yl)-N-[2-(4-quinolin-3-ylphenyl)propyl]-acetamide,
2-(2,5-Dioxoimidazolidin-4-yl)-N-(2-{4-[4(trifluoromethyl)phenoxy]phenyl}ethyl)-acetamide,
2-(2,5-Dioxoimidazolidin-4-yl)-N-{2-[4-(4-methoxyphenoxy)phenyl]ethyl}-acetamide,
2-(2,5-Dioxoimidazolidin-4-yl)-N-(2-{4-[4-(trifluoromethoxy)phenoxy]phenyl}ethyl)-acetamide,
N-{2-[4-(4-Chlorophenoxy)phenyl]ethyl}-2-(2,5-dioxoimidazolidin-4-yl)-acetamide,
N-{2-[4-(4-Acetylphenoxy)phenyl]ethyl}-2-(2,5-dioxoimidazolidin-4-yl)-acetamide,
2-(2,5-Dioxoimidazolidin-4-yl)-N-{2-[4-(pyridin-3-yloxy)phenyl]ethyl}-acetamide,
2-(2,5-Dioxoimidazolidin-4-yl)-N-(2-{4-[(6-methoxypyridin-3-yl)oxy]phenyl}ethyl)-acetamide,
N-{2-[4-(4-Cyanophenoxy)phenyl]ethyl}-2-(2,5-dioxoimidazolidin-4-yl)-acetamide,
2-(2,5-Dioxoimidazolidin-4-yl)-N-{2-[4-(4-methylphenoxy)phenyl]ethyl}-acetamide,
2-(2,5-Dioxoimidazolidin-4-yl)-N-{2-[4-(4-fluorophenoxy)phenyl]ethyl}-acetamide,
N-(2-Biphenyl-4-yl-2-hydroxy-ethyl)-2-(2,5-dioxoimidazolidin-4-yl)-acetamide,
N-[2-(1,1'-Biphenyl-4-yl)-2-methoxyethyl]-2-(2,5-dioxoimidazolidin-4-yl)-acetamide,
N-[2-(1,1'-Biphenyl-4-yl)-ethyl]-2-(2,5-dioxoimidazolidin-4-yl)-N-methylacetamide,
2-(2,5-Dioxoimidazolidin-4-yl)-N-[2-(4-phenylethynyl-piperidin-1-yl)ethyl]-acetamide,
N-{2-[(4-Bromobenzyl)oxy]ethyl}-2-(2,5-dioxoimidazolidin-4-yl)-acetamide, and pharmaceutically acceptable salts and solvates thereof.

9. A process for the preparation of a compound of formula (I) or a pharmaceutically acceptable salt or solvate thereof as defined in claim 1 which comprises, reacting a compound of formula

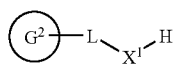
(III)

wherein $X^1$ represents an a group $NR^4$ and L, $G^2$ and $R^4$ are as defined in claim 1, formula (I), with an activated carboxylic acid of formula

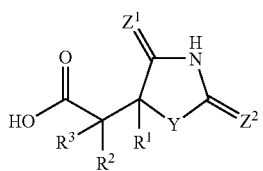
(IV)

wherein Y, $Z^1$, $Z^2$, $R^1$, $R^2$ and $R^3$ are as defined in claim 1, formula (I) and optionally forming a pharmaceutically acceptable salt or solvate.

10. A pharmaceutical composition comprising a compound of formula (I) or a pharmaceutically acceptable salt or solvate thereof as claimed in claim 1 and a pharmaceutically acceptable adjuvant, diluent or carrier.

11. A process for the preparation of a pharmaceutical composition which comprises mixing a compound of formula (I) or a pharmaceutically acceptable salt or solvate thereof as defined in claim 1 with a pharmaceutically acceptable adjuvant, diluent or carrier.

12. The method of treating asthma which comprises administering to a patient a therapeutically effective amount of a compound of formula (I) or a pharmaceutically acceptable salt or solvate thereof as claimed in claim 1.

13. A method of treating chronic obstructive pulmonary disease which comprises administering to a patient a therapeutically effective amount of a compound of formula (I) or a pharmaceutically acceptable salt or solvate thereof as claimed in claim 1.

14. A method of treating arthritis wherein the arthritis is rheumatoid arthritis or osteoarthritis which comprises administering to a patient a therapeutically effective amount of a compound of formula (I) or a pharmaceutically acceptable salt or solvate thereof as claimed in claim 1.

15. A method of treating atherosclerosis which comprises administering to a patient a therapeutically effective amount of a compound of formula (I) or a pharmaceutically acceptable salt or solvate thereof as claimed in claim 1.

16. A method of treating restenosis which comprises administering to a patient a therapeutically effective amount of a compound of formula (I) or a pharmaceutically acceptable salt or solvate thereof as claimed in claim 1.

* * * * *